(12) United States Patent
Sakamoto

(10) Patent No.: US 11,021,484 B2
(45) Date of Patent: Jun. 1, 2021

(54) COMPOUND INCLUDING NITROGEN AND ORGANIC ELECTROLUMINESCENCE DEVICE INCLUDING THE SAME

(71) Applicant: Samsung Display Co., Ltd., Yongin-si (KR)

(72) Inventor: Naoya Sakamoto, Yokohama (JP)

(73) Assignee: Samsung Display Co., Ltd., Yongin-si (KR)

(*) Notice: Subject to any disclaimer, the term of this patent is extended or adjusted under 35 U.S.C. 154(b) by 334 days.

(21) Appl. No.: 15/963,052

(22) Filed: Apr. 25, 2018

(65) Prior Publication Data

US 2019/0084992 A1   Mar. 21, 2019

(30) Foreign Application Priority Data

Sep. 20, 2017   (KR) .......................... 10-2017-0121419

(51) Int. Cl.
*C07D 487/14* (2006.01)
*C07D 471/22* (2006.01)
(Continued)

(52) U.S. Cl.
CPC ......... *C07D 487/14* (2013.01); *C07D 471/22* (2013.01); *C07D 487/22* (2013.01);
(Continued)

(58) Field of Classification Search
CPC .................................................. C07D 487/14
See application file for complete search history.

(56) References Cited

U.S. PATENT DOCUMENTS 6,579,630 B2 *  6/2003  Li ........................ H01L 51/0038
                                                            252/301.16
2014/0350243 A1  11/2014  Parham et al.
2016/0141523 A1   5/2016  Zysman-Colman et al.

FOREIGN PATENT DOCUMENTS

EP   3054498 A1   8/2016
KR   10-1540058   7/2015
(Continued)

OTHER PUBLICATIONS

Abbiati, Giorgio, et al., "Synthesis of 3,3'-disubstituted-2,2'-biindolyls through sequential palladium-catalysed reactions of 2,2,2-trifluoro-N-(2-(4-[2,2,2-trifluoro-acetylamino)-phenyl]-buta-1,3-diynyl)-phenyl)-acetamide with organic halides/triflates," Tetrahedron, 2006, vol. 62, pp. 3033-3039.
(Continued)

*Primary Examiner* — Peter F Godenschwager
(74) *Attorney, Agent, or Firm* — Lewis Roca Rothgerber Christie LLP

(57) ABSTRACT

Provided are a compound including nitrogen, represented by Formula 1, and an organic electroluminescence device including the same. In Formula 1, $A_1$ to $A_{10}$ are each independently $CR_3$ or N. The organic electroluminescence device may include a first electrode, a second electrode which is opposite to the first electrode, and a plurality of organic layers disposed between the first electrode and the second electrode, wherein the plurality of organic layers include an emission layer, and at least one organic layer among the organic layers includes the compound including nitrogen.

(Continued)

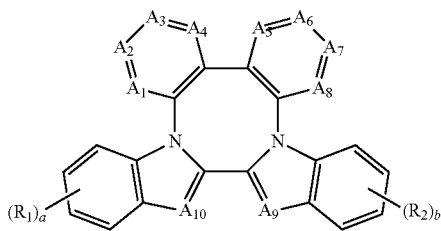

Formula 1

21 Claims, 2 Drawing Sheets

(51) Int. Cl.
  *H01L 51/50* (2006.01)
  *H01L 51/00* (2006.01)
  *C07D 487/22* (2006.01)

(52) U.S. Cl.
  CPC ...... *H01L 51/0072* (2013.01); *H01L 51/5024* (2013.01); *H01L 51/5056* (2013.01); *H01L 51/5012* (2013.01); *H01L 51/5096* (2013.01)

(56) References Cited

FOREIGN PATENT DOCUMENTS

KR  10-2016-0132582      11/2016
WO  WO 2015/083430 A1    6/2015
WO  WO 2016/182186 A1    11/2016

OTHER PUBLICATIONS

Dohi, Toshifumi, et al., "Hypervalent iodine(III): selective and efficient single-electron-transfer (SET) oxidizing agent," Tetrahedron, 2009, vol. 65, pp. 10797-10815.
Özil, Musa, et al., "Molecular docking studies and synthesis of novel bisbenzimidazole derivatives as inhibitors of α-glucosidase," Bioorganic & Medicinal Chemistry, 2016, vol. 24, pp. 5103-5114.
EPO Extended Search Report dated Jan. 25, 2019, for corresponding European Patent Application No. 18181016.9 (8 pages).

* cited by examiner

COMPOUND INCLUDING NITROGEN AND ORGANIC ELECTROLUMINESCENCE DEVICE INCLUDING THE SAME

CROSS-REFERENCE TO RELATED APPLICATION

This application claims priority to and the benefit of Korean Patent Application No. 10-2017-0121419, filed on Sep. 20, 2017, the entire content of which is incorporated herein by reference.

BACKGROUND

The present disclosure herein relates to a compound including nitrogen and an organic electroluminescence device including the same.

The development of an organic electroluminescence display as an image display is being actively conducted. The organic electroluminescence display is different from a liquid crystal display and is a so called self-luminescent display that displays an image via the recombination of holes and electrons injected from a first electrode and a second electrode in an emission layer and via light emission from a luminescent material including an organic compound in the emission layer.

As an organic electroluminescence device, an organic device including, for example, a first electrode, a hole transport layer disposed on the first electrode, an emission layer disposed on the hole transport layer, an electron transport layer disposed on the emission layer, and a second electrode disposed on the electron transport layer has been prepared. Holes are injected from the first electrode, and the injected holes move via the hole transport layer and are injected into the emission layer. Meanwhile, electrons are injected from the second electrode, and the injected electrons move via the electron transport layer and are injected into the emission layer. The holes and electrons injected into the emission layer recombine to produce excitons in the emission layer. The organic electroluminescence device emits light using light generated by the transition of the excitons to a ground state. In addition, an embodiment of the configuration of the organic electroluminescence device is not limited thereto, but various modifications may be possible.

SUMMARY

The present disclosure provides a compound including nitrogen and an organic electroluminescence device including the same.

An embodiment of the present disclosure provides a compound including nitrogen, represented by the following Formula 1:

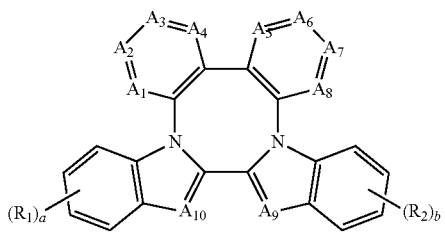

Formula 1

In Formula 1, $A_1$ to $A_{10}$ are each independently $CR_3$ or N, $R_1$ to $R_3$ are each independently a hydrogen atom, a deuterium atom, a halogen atom, a cyano group, a substituted or unsubstituted amino group, a substituted or unsubstituted silyl group, a substituted or unsubstituted phosphine group, a substituted or unsubstituted alkyl group having 1 to 20 carbon atoms, a substituted or unsubstituted aryl group having 6 to 30 carbon atoms for forming a ring, or a substituted or unsubstituted heteroaryl group having 2 to 30 carbon atoms for forming a ring, and "a" and "b" are each independently an integer of 0 to 4.

In an embodiment, the number of nitrogen atoms (N) among $A_1$ to $A_8$ may be 0, 1, or 2.

In an embodiment, $A_9$ and $A_{10}$ may be the same.

In an embodiment, at least one chosen from $A_1$ to $A_8$ may be $CR_3$ or N, and $R_3$ may be a fluorine atom, a cyano group, a substituted or unsubstituted arylamino group, a substituted or unsubstituted triphenylsilyl group, a substituted or unsubstituted diphenylphosphine oxide group, a substituted or unsubstituted alkyl group having 1 to 5 carbon atoms, a substituted or unsubstituted phenyl group, a substituted or unsubstituted pyridine group, a substituted or unsubstituted triazine group, a substituted or unsubstituted carbazole group, a substituted or unsubstituted dibenzofuran group, or a substituted or unsubstituted dibenzothiophene group.

In an embodiment, $A_9$ and $A_{10}$ may be nitrogen atoms (N).

In an embodiment, $A_9$ and $A_{10}$ may be each independently $CR_3$, and $R_3$ may be a hydrogen atom, a substituted or unsubstituted alkyl group having 1 to 5 carbon atoms, or a substituted or unsubstituted phenyl group.

In an embodiment, "a" and "b" may be 0.

In an embodiment, at least one of "a" or "b" may be 1 or more, and at least one of $R_1$ or $R_2$ may be a fluorine atom, a cyano group, a substituted or unsubstituted arylamino group, a substituted or unsubstituted triphenylsilyl group, a substituted or unsubstituted diphenylphosphine oxide group, a substituted or unsubstituted phenyl group, a substituted or unsubstituted pyridine group, a substituted or unsubstituted triazine group, a substituted or unsubstituted carbazole group, a substituted or unsubstituted dibenzofuran group, or a substituted or unsubstituted dibenzothiophene group.

In an embodiment of the present disclosure, an organic electroluminescence device includes a first electrode, a second electrode which is opposite to the first electrode, and a plurality of organic layers disposed between the first electrode and the second electrode, wherein the plurality of organic layers include an emission layer, and at least one organic layer among the organic layers includes the compound including nitrogen according to an embodiment of the present disclosure.

In an embodiment, the emission layer may include the compound including nitrogen according to an embodiment of the present disclosure.

In an embodiment, the emission layer may include a host and a dopant, and the host may include the compound including nitrogen according to an embodiment of the present disclosure.

In an embodiment, the organic layers may include a hole transport region disposed between the first electrode and the emission layer, and an electron transport region disposed between the emission layer and the second electrode, and the hole transport region may include the compound including nitrogen according to an embodiment of the present disclosure.

In an embodiment, the first electrode and the second electrode each independently include at least one selected from Ag, Mg, Cu, Al, Pt, Pd, Au, Ni, Nd, Ir, Cr, Li, Ca, LiF/Ca, LiF/Al, Mo, Ti, In, Sn, and Zn, or a compound of two or more selected from them, a mixture of two or more selected from them, or oxides of one or more selected from them.

BRIEF DESCRIPTION OF THE FIGURES

The accompanying drawings are included to provide a further understanding of the subject matter of the present disclosure, and are incorporated in and constitute a part of this specification. The drawings illustrate exemplary embodiments of the present disclosure and, together with the description, serve to explain principles of embodiments of the present disclosure. In the drawings.

DETAILED DESCRIPTION

Figure 1:
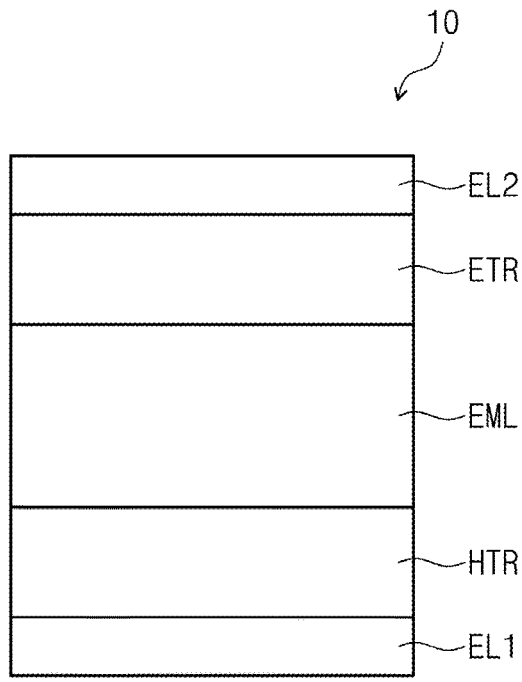
FIG. 1 is a cross-sectional view schematically illustrating an organic electroluminescence device according to an embodiment of the present disclosure.

The above objects, other objects, features and/or advantages of the present disclosure will be readily understood from exemplary embodiments described herein with reference to the accompanying drawings. The present disclosure may, however, be embodied in different forms and should not be construed as limited to the embodiments set forth herein.

Like reference numerals refer to like elements for explaining each drawing. In the drawings, the sizes of elements may be enlarged for clarity of the present disclosure. It will be understood that, although the terms first, second, etc. may be used herein to describe various elements, these elements should not be limited by these terms. These terms are only used to distinguish one element from another element. For example, a first element discussed below could be termed a second element, and similarly, a second element could be termed a first element. As used herein, the singular forms are intended to include the plural forms as well, unless the context clearly indicates otherwise.

It will be further understood that the terms "comprises" or "comprising," when used in this specification, specify the presence of stated features, numerals, steps, operations, elements, parts, or a combination thereof, but do not preclude the presence or addition of one or more other features, numerals, steps, operations, elements, parts, or a combination thereof. It will also be understood that when a layer, a film, a region, a plate, etc. is referred to as being "on" another part, it can be "directly on" the other part, or intervening layers may also be present. On the contrary, when a layer, a film, a region, a plate, etc. is referred to as being "under" another part, it can be "directly under" the other part, or intervening layers may also be present.

In the present disclosure,

means a part to be coupled or connected.

In the present disclosure, "substituted or unsubstituted" may mean substituted with at least one substituent selected from the group consisting of a deuterium atom, a halogen atom, a cyano group, a nitro group, an amino group, a silyl group, a boron group, a phosphine group, an alkyl group, an alkenyl group, an aryl group, and a heterocycle, or unsubstituted. In addition, each of the substituent illustrated above may be substituted or unsubstituted. For example, a biphenyl group may be interpreted as an aryl group, or a phenyl group substituted with a phenyl group.

In the present disclosure, a halogen atom may include a fluorine atom, a chlorine atom, a bromine atom, or an iodine atom.

In the present disclosure, the alkyl group may have a linear or branched chain or a cycle shape. The carbon number of the alkyl group may be 1 to 30, 1 to 20, 1 to 10, or 1 to 6. Examples of the alkyl group may include methyl, ethyl, n-propyl, isopropyl, n-butyl, s-butyl, t-butyl, i-butyl, 2-ethylbutyl, 3,3-dimethylbutyl, n-pentyl, pentyl, neopentyl, t-pentyl, cyclopentyl, 1-methylpentyl, 3-methylpentyl, 2-ethylpentyl, 4-methyl-2-pentyl, n-hexyl, 1-methylhexyl, 2-ethyihexyl, 2-butylhexyl, cyclohexyl, 4-methylcyclohexyl, 4-t-butylcyclohexyl, n-heptyl, 1-methylheptyl, 2,2-dimethylheptyl, 2-ethylheptyl, 2-butylheptyl, n-octyl, t-octyl, 2-ethyloctyl, 2-butyloctyl, 2-hexyloctyl, 3,7-dimethyloctyl, cyclooctyl, n-nonyl, n-decyl, adamantyl, 2-ethyldecyl, 2-butyldecyl, 2-hexyldecyl, 2-octyldecyl, n-undecyl, n-dodecyl, 2-ethyldodecyl, 2-butyldodecyl, 2-hexyldodecyl, 2-octyldodecyl, n-tridecyl, n-tetradecyl, n-pentadecyl, n-hexadecyl, 2-ethylhexadecyl, 2-butylhexadecyl, 2-hexyihexadecyl, 2-octylhexadecyl, n-heptadecyl, n-octadecyl, n-nonadecyl, n-eicosyl, 2-ethyl eicosyl, 2-butyl eicosyl, 2-hexyl eicosyl, 2-octyl eicosyl, n-henicosyl, n-docosyl, n-tricosyl, n-tetracosyl, n-pentacosyl, n-hexacosyl, n-heptacosyl, n-octacosyl, n-nonacosyl, n-triacontyl, etc., without limitation.

In the present disclosure, the aryl group means an optional functional group or substituent derived from aromatic cyclic hydrocarbon. The aryl group may be monocyclic aryl group or polycyclic aryl group. The carbon number of the aryl group for forming a ring may be 6 to 30, 6 to 20, or 6 to 15. Examples of the aryl group may include phenyl, naphthyl, fluorenyl, anthracenyl, phenanthryl, biphenyl, terphenyl, quaterphenyl, quinqphenyl, sexiphenyl, biphenylene, triphenylene, pyrenyl, benzofluoranthenyl, chrysenyl, etc., without limitation.

In the present disclosure, fluorenyl may be substituted, or two substituents may be combined with each other to form a spiro structure. Examples of the substituted fluorenyl are as follows. However, embodiments of the present disclosure are not limited thereto.

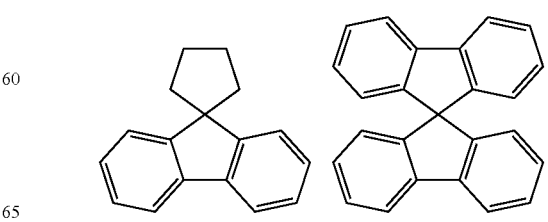

-continued

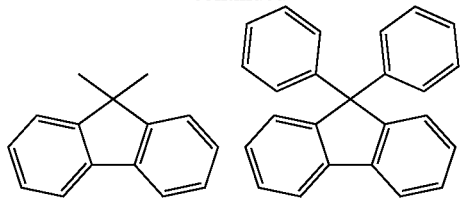

In the present disclosure, the heteroaryl group may be heteroaryl including at least one of O, N, P, Si or S as a heteroatom. When the heteroaryl group includes two heteroatoms, two heteroatoms may be the same or different from each other. The carbon number of the heteroaryl group for forming a ring may be 2 to 30, or 2 to 20. The heteroaryl group may be monocyclic heteroaryl group or polycyclic heteroaryl group. The heteroaryl group may have a structure, for example of two rings or three rings. Examples of the heteroaryl may include thiophene, furan, pyrrole, imidazole, thiazole, oxazole, oxadiazole, triazole, pyridine, bipyridine, pyrimidine, triazine, triazole, acridyl, pyridazine, pyrazinyl, quinoline, quinazoline, quinoxaline, phenoxazine, phthalazine, pyrido pyrimidine, pyrido pyrazine, pyrazino pyrazine, isoquinoline, indole, carbazole, N-arylcarbazole, N-heteroaryl carbazole, N-alkyl carbazole, benzoxazole, benzoimidazole, benzothiazole, benzocarbazole, benzothiophene, dibenzothiophene, thienothiophene, benzofuran, phenanthroline, thiazole, isooxazole, oxadiazole, thiadiazole, phenothiazine, dibenzosilole, dibenzofuran, etc., without limitation.

In the present disclosure, the silyl group may include alkylsilyl group and arylsilyl group. Examples of the silyl group may include trimethylsilyl, triethylsilyl, t-butyldimethylsilyl, vinyldimethylsilyl, propyldimethylsilyl, triphenylsilyl, diphenylsilyl, phenylsilyl, etc., without limitation.

In the present disclosure, the boron group may include alkyl boron group and aryl boron group. Examples of the boron group may include trimethylboron, triethylboron, t-butyldimethyl boron, triphenylboron, diphenylboron, phenylboron, etc., without limitation.

In the present disclosure, the alkenyl group may be linear or branched. The carbon number of the alkenyl group is not specifically limited, but may be 2 to 30, 2 to 20, or 2 to 10. Examples of the alkenyl group may include vinyl, 1-butenyl, 1-pentenyl, 1,3-butadienyl aryl, styrenyl, styrylvinyl, etc., without limitation.

In the present disclosure, the carbon number of the amino group is not specifically limited, but may be 1 to 30. The amino group may include an alkylamino group and an arylamino group. Examples of the amino group may include a methylamino group, a dimethylamino group, a phenylamino group, a diphenylamino group, a naphthylamino group, a 9-methyl-anthracenylamino group, a triphenylamino group, etc., without limitation.

In the present disclosure, the phosphine group may be a phosphine oxide group or a phosphine sulfide group. For example, the phosphine group may be a phosphine oxide group substituted with an aryl group.

First, the compound including nitrogen according to an embodiment of the present disclosure will be explained.

The compound including nitrogen according to an embodiment of the present disclosure is represented by Formula 1 below.

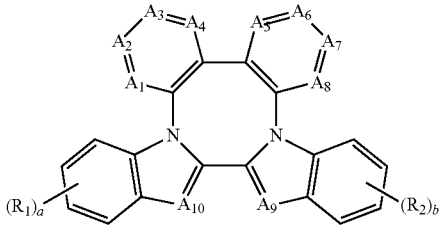

Formula 1

In Formula 1, $A_1$ to $A_{10}$ are each independently $CR_3$ or N, $R_1$ to $R_3$ are each independently a hydrogen atom, a deuterium atom, a halogen atom, a cyano group, a substituted or unsubstituted amino group, a substituted or unsubstituted silyl group, a substituted or unsubstituted phosphine group, a substituted or unsubstituted alkyl group having 1 to 20 carbon atoms, a substituted or unsubstituted aryl group having 6 to 30 carbon atoms for forming a ring, or a substituted or unsubstituted heteroaryl group having 2 to 30 carbon atoms for forming a ring, and "a" and "b" are each independently an integer of 0 to 4.

If "a" is 2 or more, a plurality of $R_1$ groups may be the same or different from each other. If "b" is 2 or more, a plurality of $R_2$ groups may be the same or different from each other.

The number of nitrogen atoms (N) among $A_1$ to $A_8$ may be 0, 1, or 2. However, an embodiment of the present disclosure is not limited thereto.

$A_9$ and $A_{10}$ may be the same. For example, $A_9$ and $A_{10}$ may be nitrogen atoms (N). In another embodiment, $A_9$ and $A_{10}$ may be $CR_3$, and $R_3$ may be the same. If $A_9$ and $A_{10}$ are $CR_3$, adjacent two $R_3$ groups may not be combined to each other to form a ring.

$A_9$ and $A_{10}$ may be each independently $CR_3$, and $R_3$ may be a hydrogen atom, a substituted or unsubstituted alkyl group having 1 to 5 carbon atoms, or a substituted or unsubstituted phenyl group.

$A_9$ and $A_{10}$ may be each independently $CR_3$, and $R_3$ may be a hydrogen atom, a substituted or unsubstituted methyl group, or an unsubstituted phenyl group.

At least one chosen from $A_1$ to $A_8$ may be $CR_3$ or N, and $R_3$ may be a fluorine atom, a cyano group, a substituted or unsubstituted arylamino group, a substituted or unsubstituted arylsilyl group, a substituted or unsubstituted phosphine oxide group, a substituted or unsubstituted alkyl group having 1 to 5 carbon atoms, a substituted or unsubstituted monocyclic aryl group, a substituted or unsubstituted monocyclic heteroaryl group including nitrogen, or a substituted or unsubstituted polycyclic heteroaryl group.

At least one chosen from $A_1$ to $A_8$ may be $CR_3$ or N, and $R_3$ may be a fluorine atom, a cyano group, a substituted or unsubstituted arylamino group, a substituted or unsubstituted triphenylsilyl group, a substituted or unsubstituted diphenylphosphine oxide group, a substituted or unsubstituted alkyl group having 1 to 5 carbon atoms, a substituted or unsubstituted phenyl group, a substituted or unsubstituted pyridine group, a substituted or unsubstituted triazine group, a substituted or unsubstituted carbazole group, a substituted or unsubstituted dibenzofuran group, or a substituted or unsubstituted dibenzothiophene group. Examples of the substituted or unsubstituted alkyl group having 1 to 5 carbon atoms include a methyl group, an n-butyl group, a t-butyl group, etc.

"a" and "b" may be 0. However, an embodiment of the present disclosure is not limited thereto. At least one of "a"

or "b" may be 1 or more. In this case, at least one of $R_1$ or $R_2$ may be a fluorine atom, a cyano group, a substituted or unsubstituted arylamino group, a substituted or unsubstituted arylsilyl group, a substituted or unsubstituted phosphine oxide group, a substituted or unsubstituted monocyclic aryl group, a substituted or unsubstituted monocyclic heteroaryl group including nitrogen, or a substituted or unsubstituted polycyclic heteroaryl group. For example, at least one of $R_1$ or $R_2$ may be a fluorine atom, a cyano group, a substituted or unsubstituted arylamino group, a substituted or unsubstituted triphenylsilyl group, a substituted or unsubstituted diphenylphosphine oxide group, a substituted or unsubstituted phenyl group, a substituted or unsubstituted pyridine group, a substituted or unsubstituted triazine group, a substituted or unsubstituted carbazole group, a substituted or unsubstituted dibenzofuran group, or a substituted or unsubstituted dibenzothiophene group.

The compound including nitrogen, represented by Formula 1 may have a line symmetrical structure (e.g., may be symmetrical about a line passing through a center of the structure). However, an embodiment of the present disclosure is not limited thereto. For example, the compound including nitrogen, represented by Formula 1 may have an asymmetrical structure.

$R_1$ to $R_3$ may be each independently represented by a hydrogen atom, a fluorine atom, a cyano group, a methyl group, a t-butyl group, or one of the following structures:

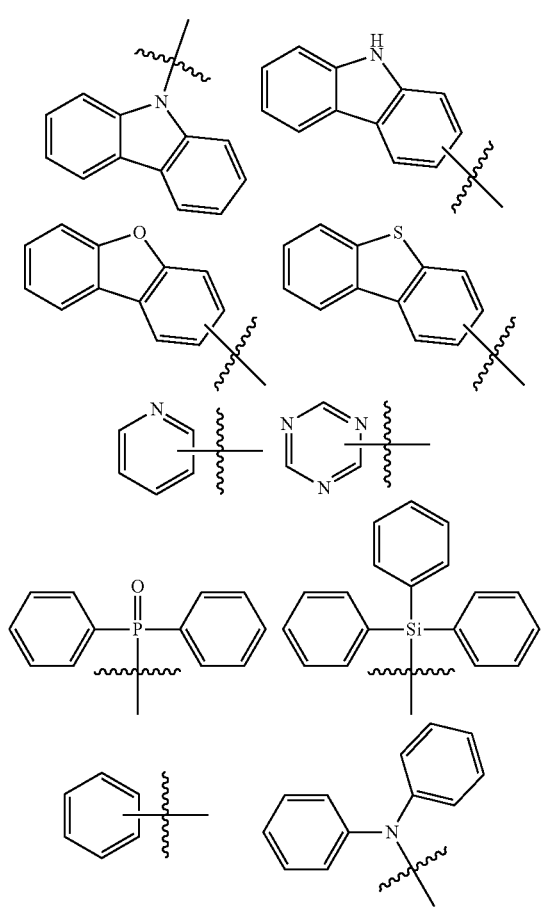

Each of the structures may be substituted or unsubstituted, and if substituted, a substituent may be at least one of an alkyl group, an aryl group, or a heteroaryl group. For example, at least one chosen from $R_1$ to $R_3$ may be a triazine group, and the triazine group may be substituted with a phenyl group, and for example, may be represented by the following structure:

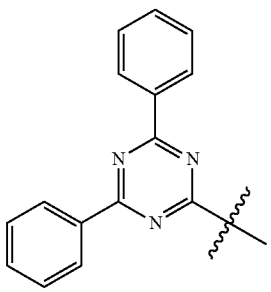 [SMILES: *c1nc(-c2ccccc2)nc(-c2ccccc2)n1]

The compound including nitrogen, represented by Formula 1 according to an embodiment of the present disclosure may be any one selected from the compounds represented in the following Compound Group 1. However, an embodiment of the present disclosure is not limited thereto.

Compound Group 1

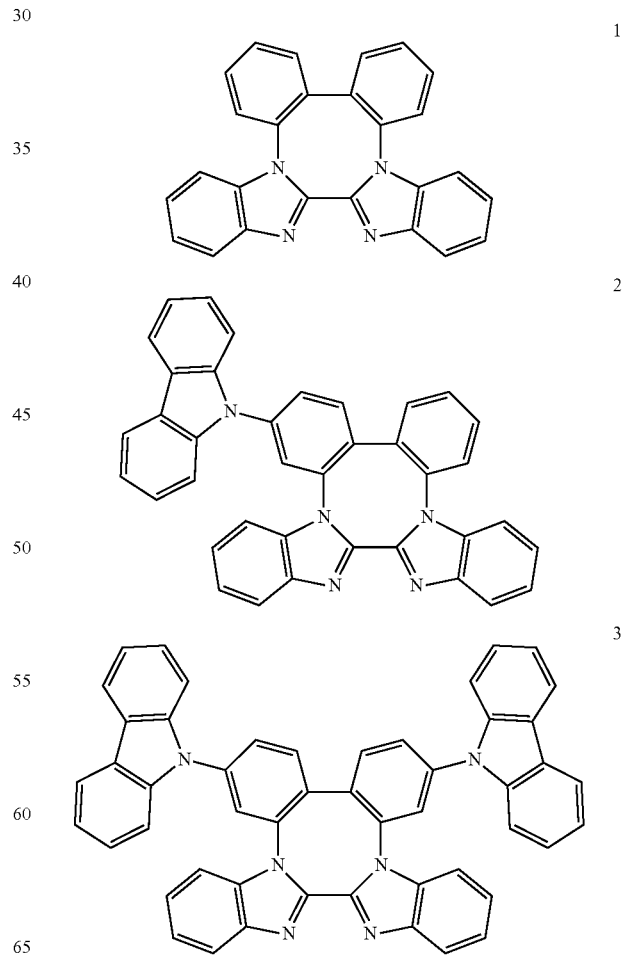

4
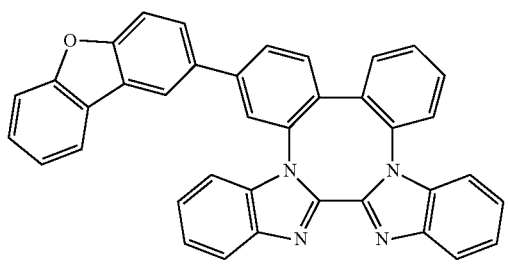
5
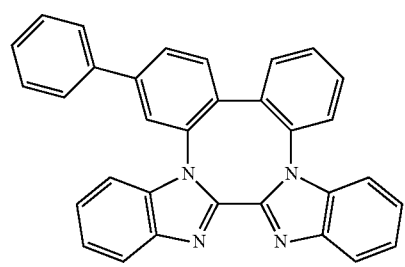
6
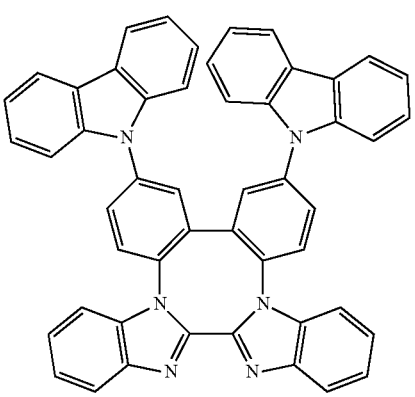
7
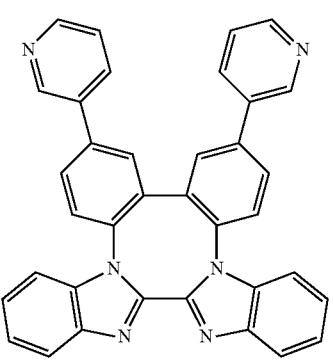
8
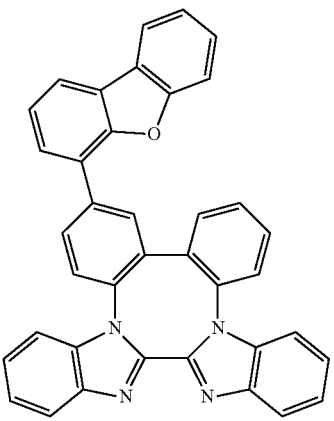
9
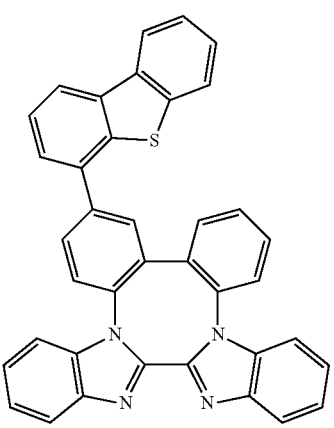
10
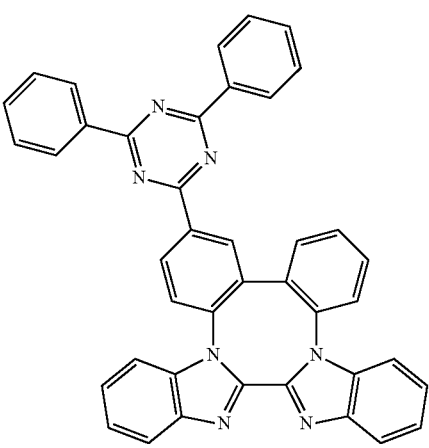
11
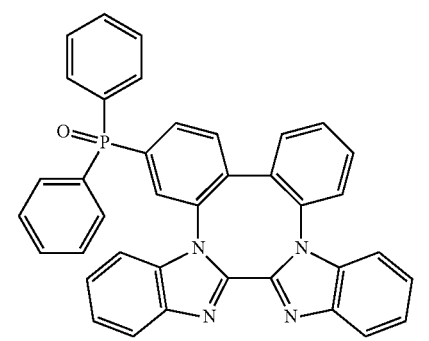

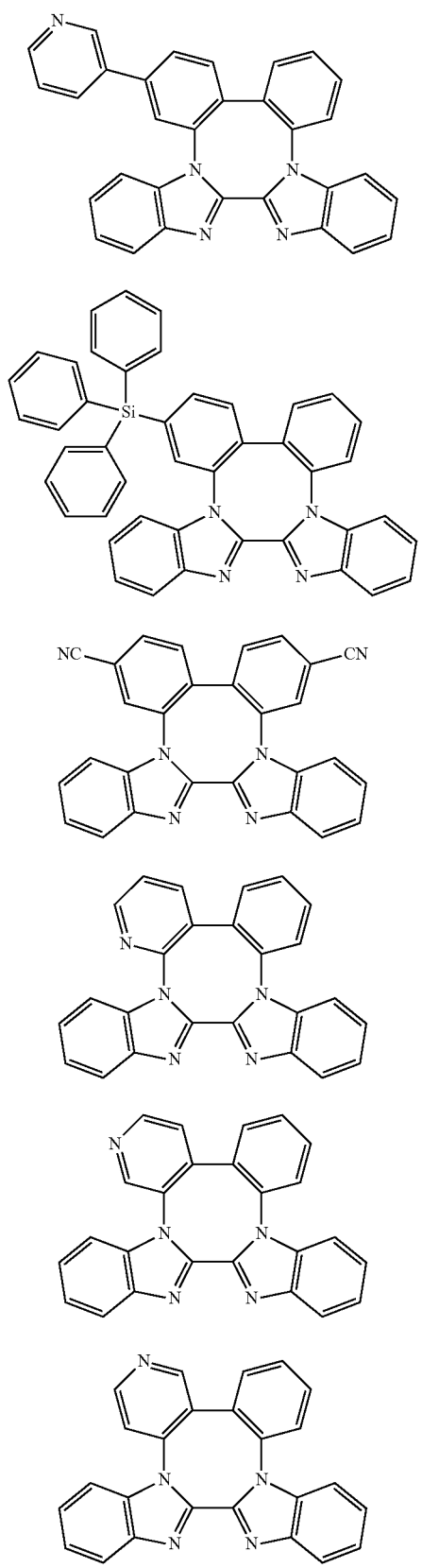
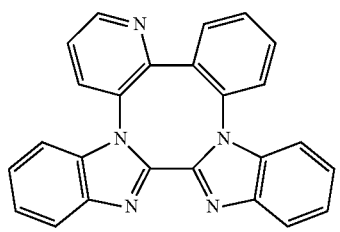
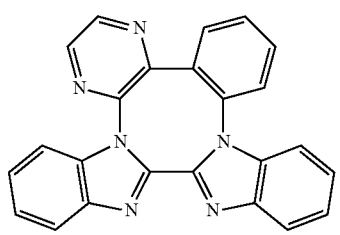
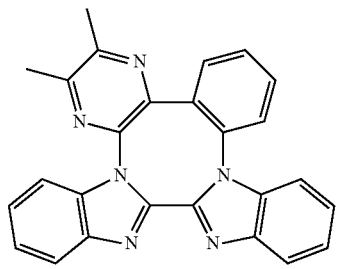
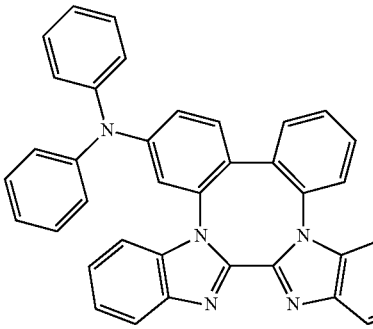
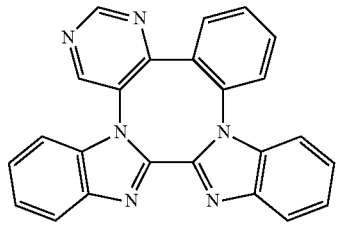
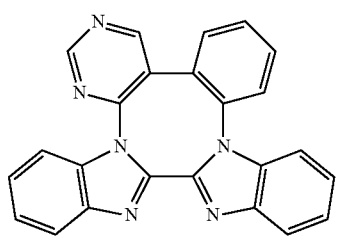

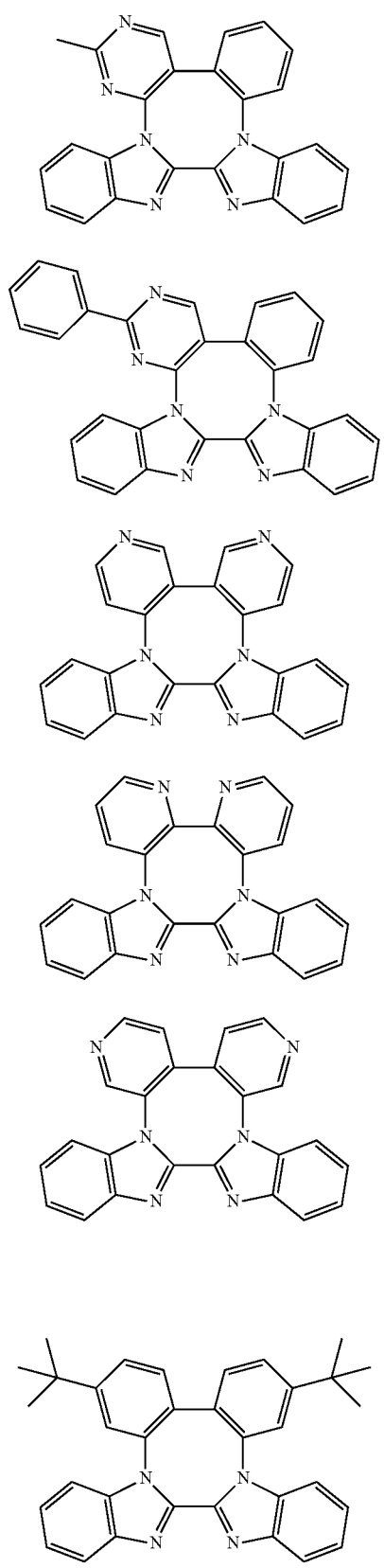
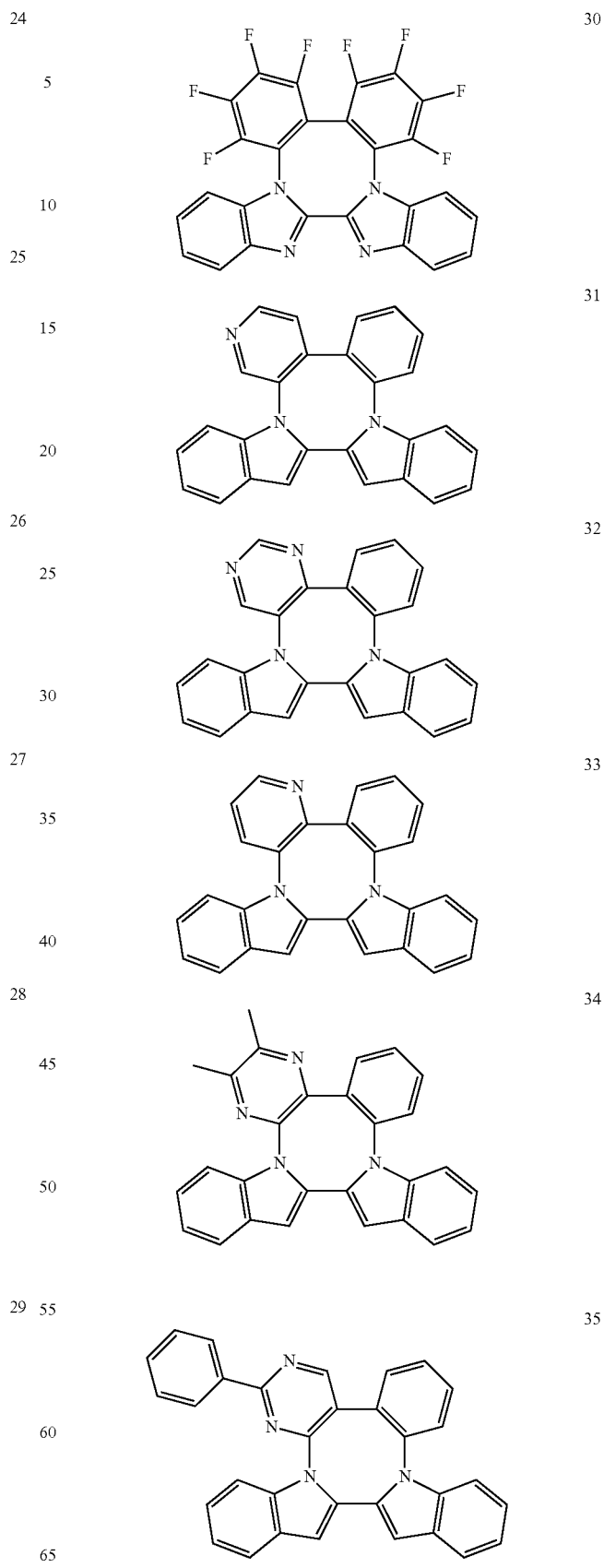

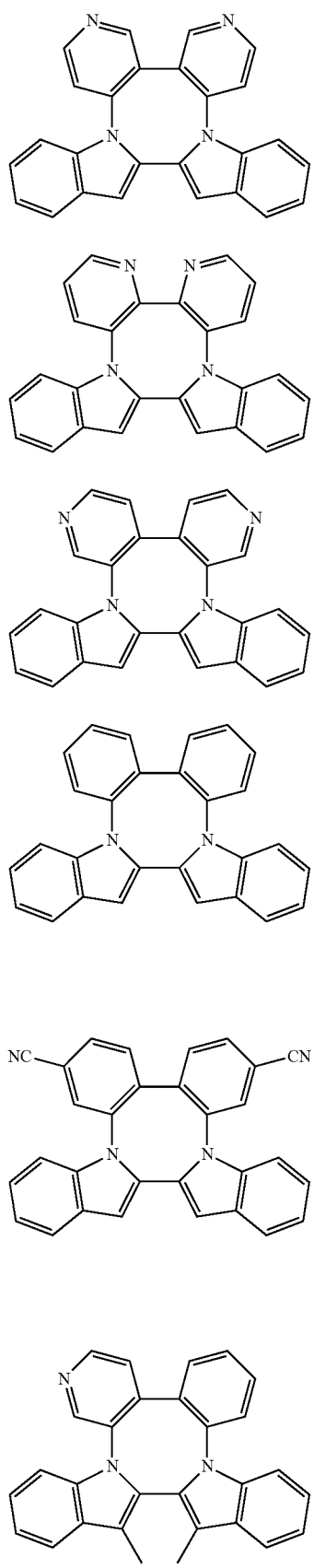
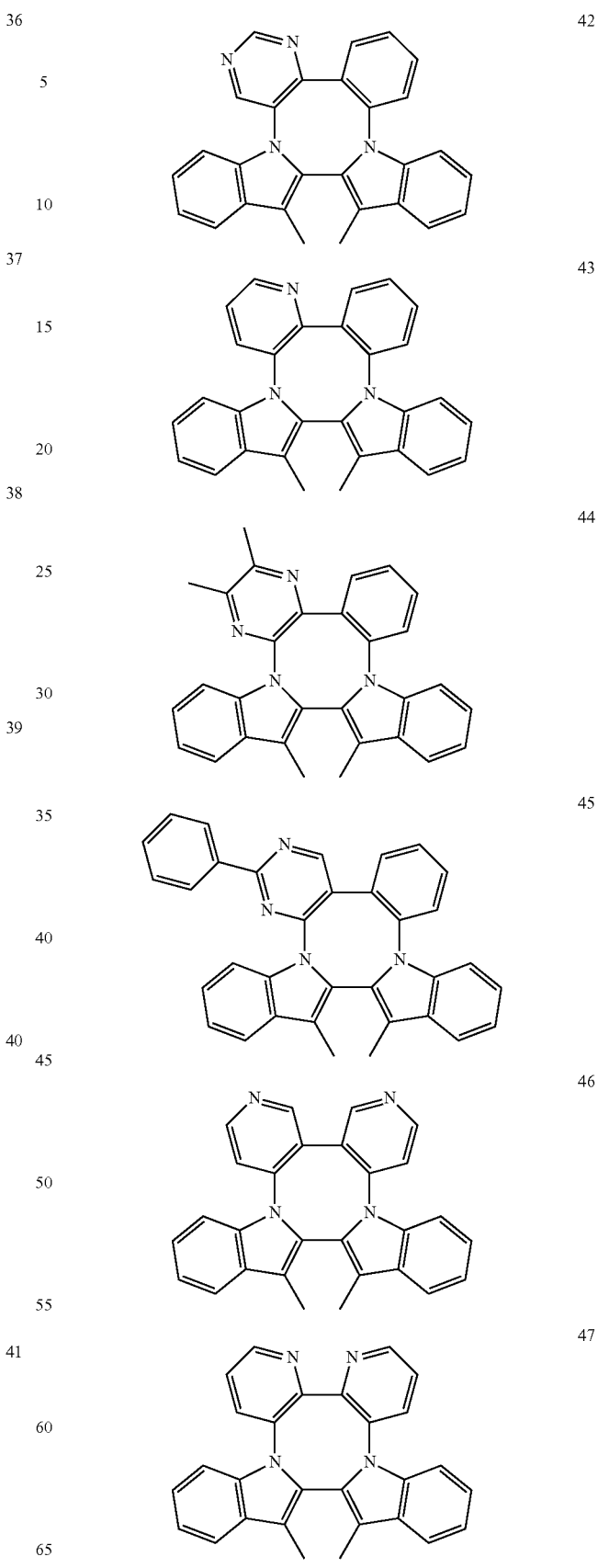

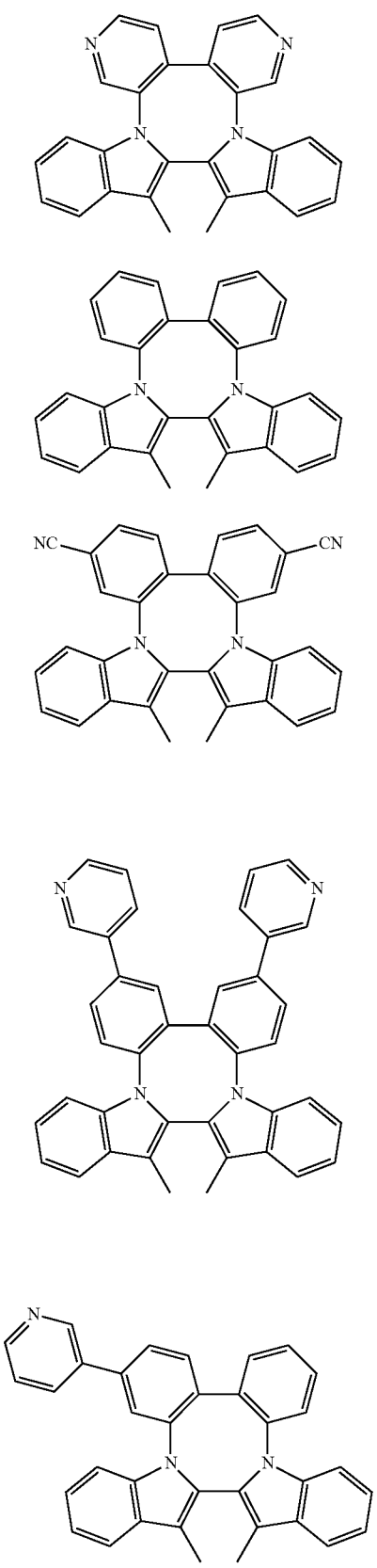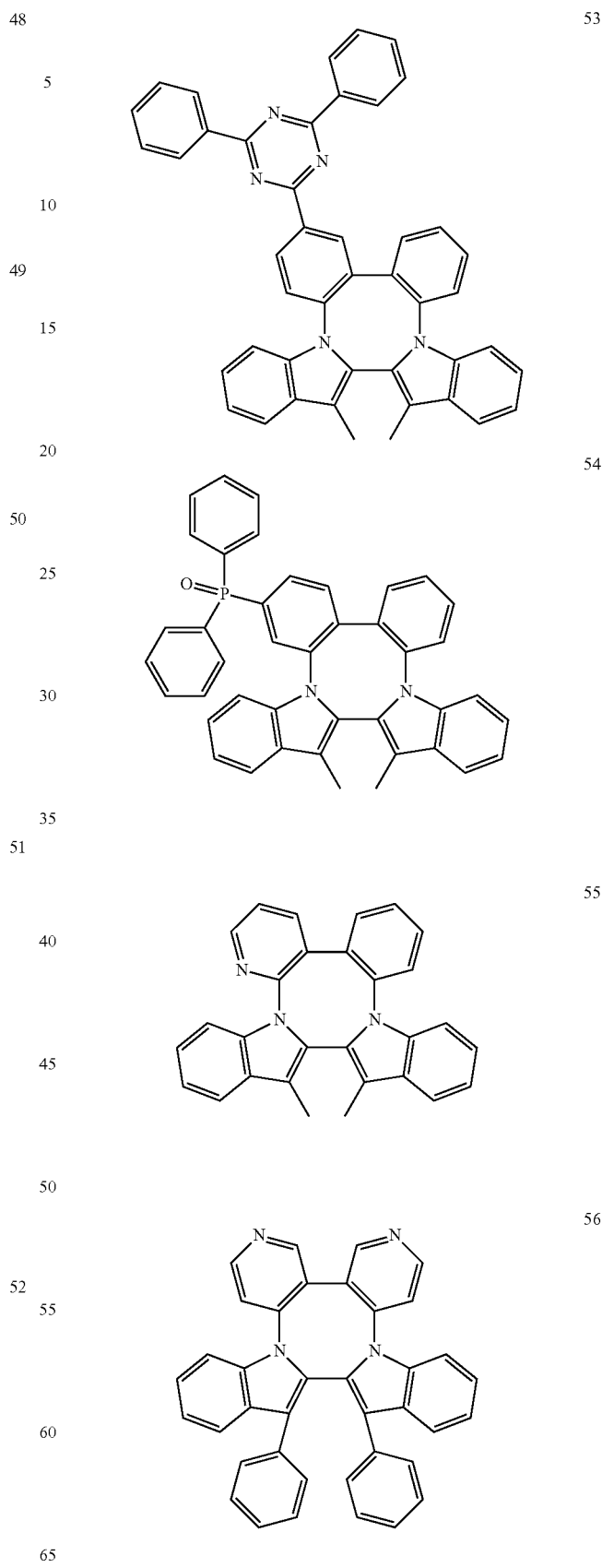

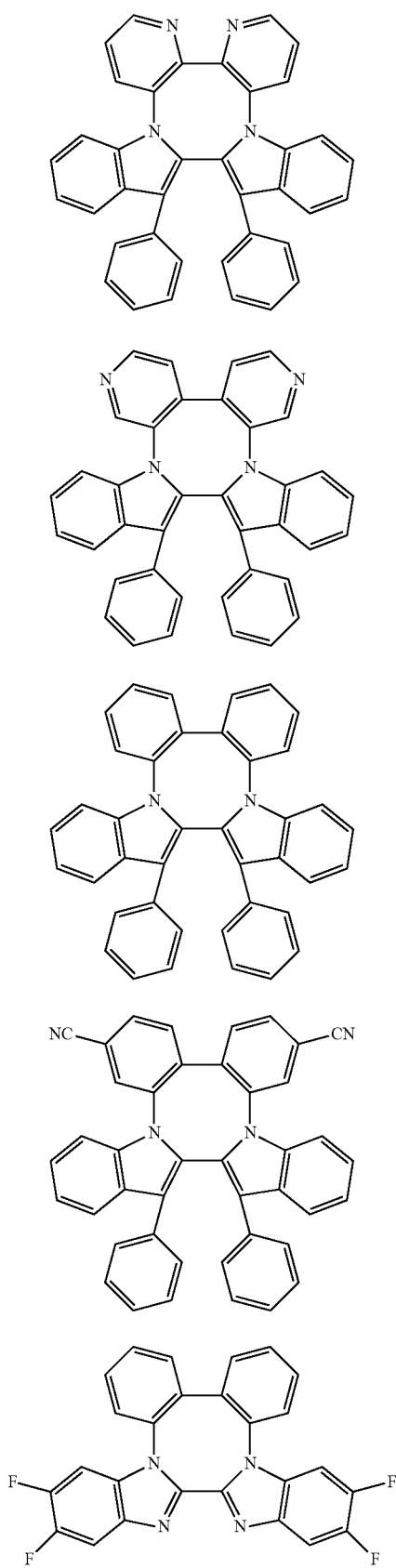
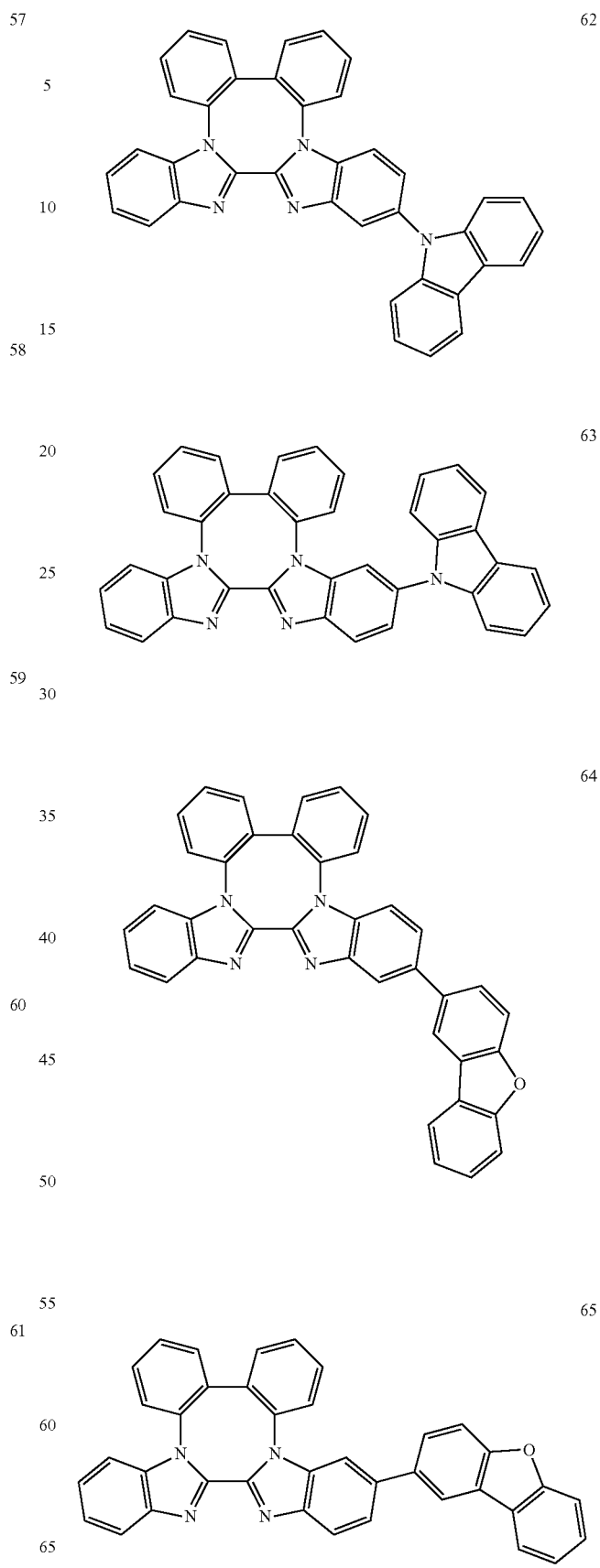

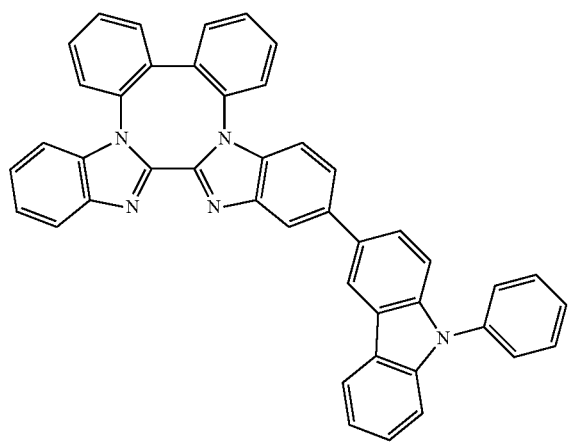
66
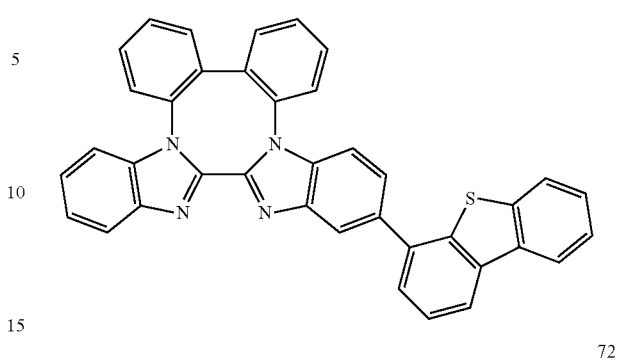
71
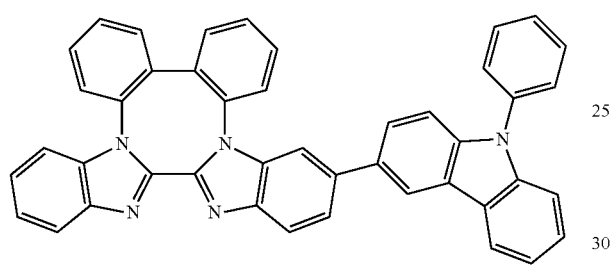
67
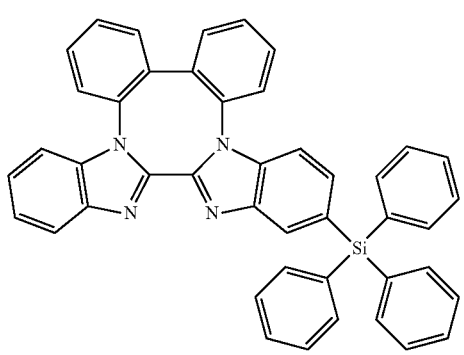
72
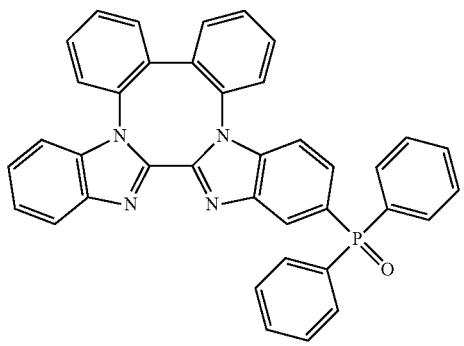
73
68
69
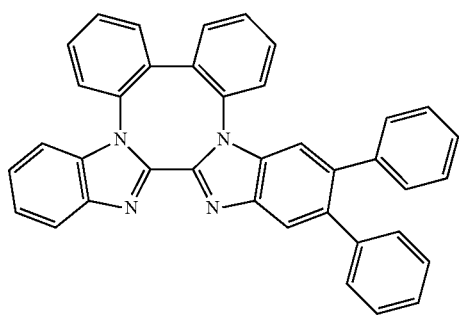
74
70
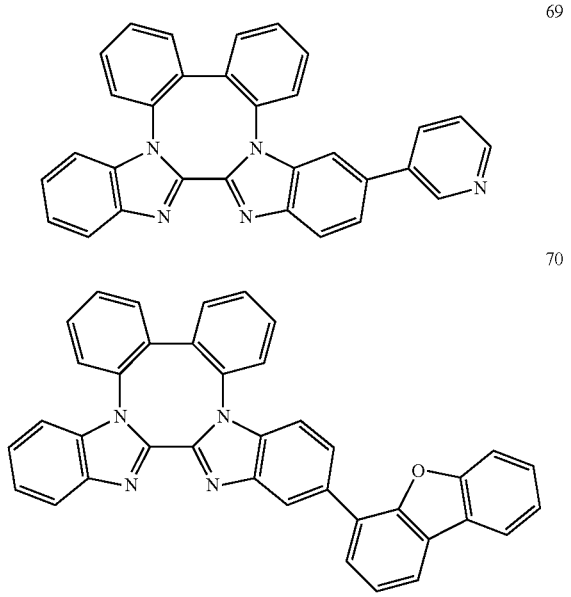
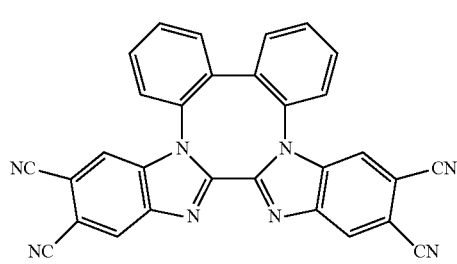
75

76

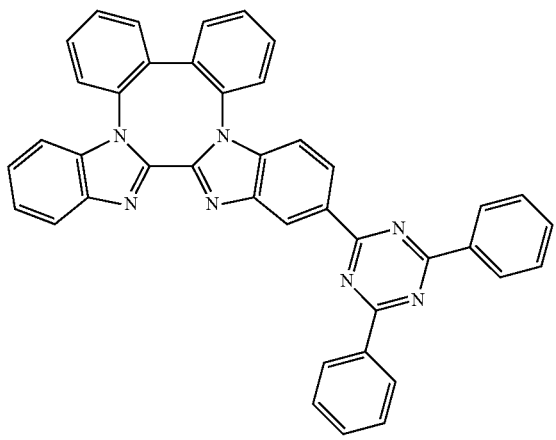

77

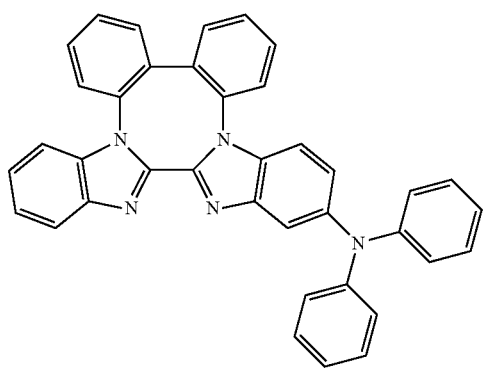

78

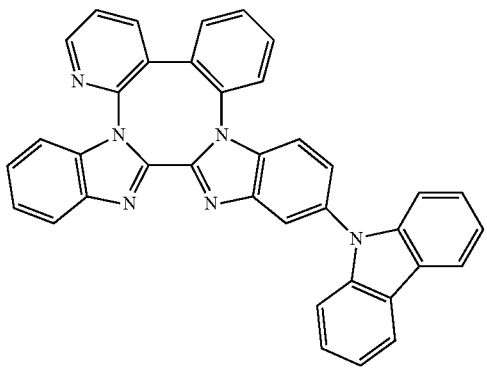

79

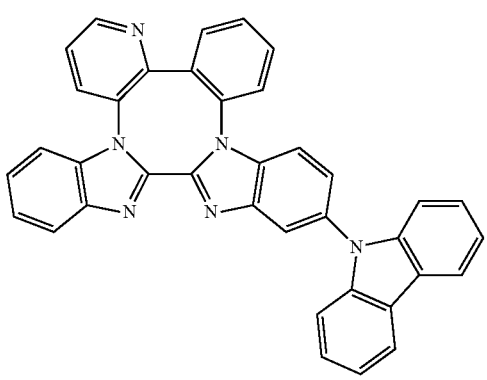

80

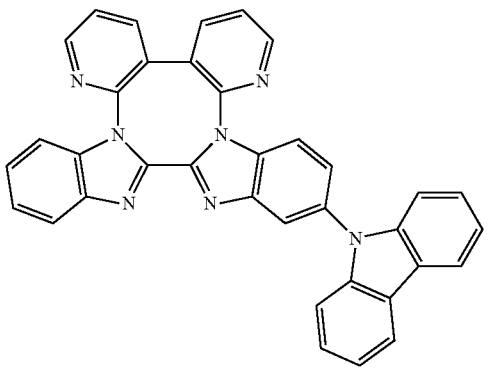

The compound including nitrogen according to an embodiment of the present disclosure has a high triplet energy level, and thus, when used in an organic electroluminescence device, efficiency may be increased. In addition, since the compound has a high triplet energy level, a difference between a singlet energy level and a triplet energy level is decreased, and the compound may be applied as a material for thermally activated delayed fluorescence.

Hereinafter, an organic electroluminescence device according to an embodiment of the present disclosure will be explained in further detail. The explanation will be mainly with regard to the difference from that for the compound including nitrogen according to an embodiment of the present disclosure, and the unexplained part will follow the above-description on the compound including nitrogen according to an embodiment of the present disclosure.

The organic electroluminescence device according to an embodiment of the present disclosure includes the above-described compound including nitrogen according to an embodiment of the present disclosure.

Figure 2:
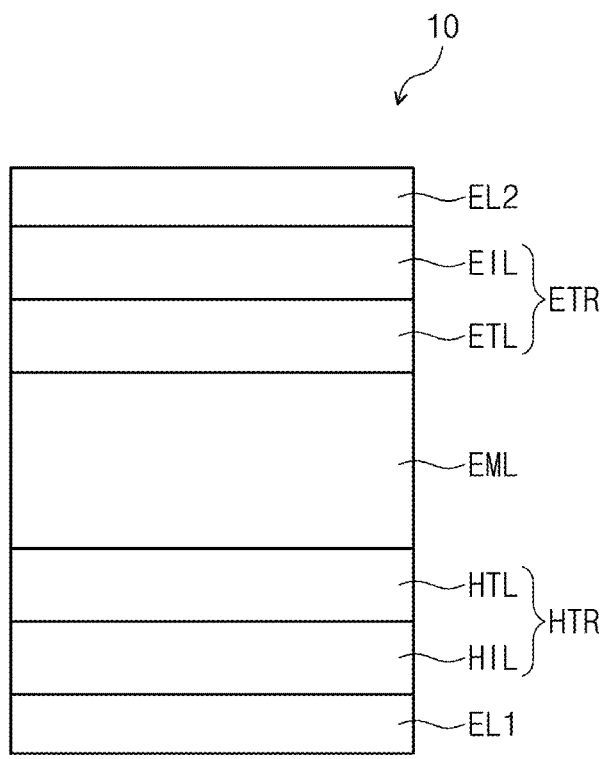
FIG. 2 is a cross-sectional view schematically illustrating an organic electroluminescence device according to an embodiment of the present disclosure.
Figure 3:
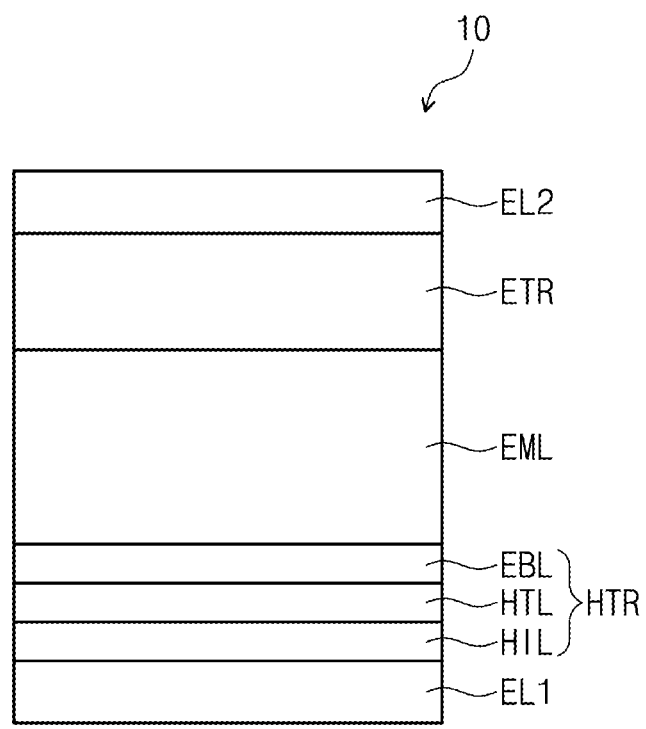
FIG. 3 is a cross-sectional view schematically illustrating an organic electroluminescence device according to an embodiment of the present disclosure.

FIG. 1 is a cross-sectional view schematically illustrating an organic electroluminescence device according to an embodiment of the present disclosure. FIG. 2 is a cross-sectional view schematically illustrating an organic electroluminescence device according to an embodiment of the present disclosure. FIG. 3 is a cross-sectional view schematically illustrating an organic electroluminescence device according to an embodiment of the present disclosure.

Referring to FIGS. 1 to 3, an organic electroluminescence device 10 according to an embodiment of the present disclosure may include a first electrode EL1, a hole transport region HTR, an emission layer EML, an electron transport region ETR, and a second electrode EL2.

The first electrode EL1 and the second electrode EL2 are oppositely disposed, and between the first electrode EL1 and the second electrode EL2, a plurality of organic layers may be disposed. The plurality of the organic layers may include a hole transport region HTR, an emission layer EML and an electron transport region ETR.

The organic electroluminescence device 10 according to an embodiment of the present disclosure may include the compound including nitrogen according to an embodiment of the present disclosure in at least one organic layer among the plurality of the organic layers disposed between the first electrode EL1 and the second electrode EL2. For example, the compound including nitrogen according to an embodiment of the present disclosure may be included in the emission layer EML. However, an embodiment of the present disclosure is not limited thereto.

The first electrode EL1 has conductivity. The first electrode EL1 may be a pixel electrode or an anode. The first electrode EL1 may be a transmissive electrode, a transflective electrode, or a reflective electrode. If the first electrode EL1 is the transmissive electrode, the first electrode EL1 may be formed using a transparent metal oxide such as indium tin oxide (ITO), indium zinc oxide (IZO), zinc oxide (ZnO), or indium tin zinc oxide (ITZO). If the first electrode EL1 is the transflective electrode or reflective electrode, the first electrode EL1 may include Ag, Mg, Cu, Al, Pt, Pd, Au, Ni, Nd, Ir, Cr, Li, Ca, LiF/Ca, LiF/Al, Mo, Ti, a compound thereof, or a mixture thereof (for example, a mixture of Ag and Mg). Also, the first electrode EL1 may include a plurality of layers including the reflective layer or transflective layer formed using the above materials, or a transparent layer formed using ITO, IZO, ZnO, or ITZO. For example, the first electrode EL1 may have a three-layer structure of ITO/Ag/ITO. However, an embodiment of the present disclosure is not limited thereto.

The thickness of the first electrode EL1 may be from about 1,000 Å to about 10,000 Å, for example, from about 1,000 Å to about 3,000 Å.

The hole transport region HTR is provided on the first electrode EL1. The hole transport region HTR may include at least one of a hole injection layer HIL, a hole transport layer HTL, a hole buffer layer, or an electron blocking layer.

The hole transport region HTR may have a single layer formed using a single material, a single layer formed using a plurality of different materials, or a multilayer structure including a plurality of layers formed using a plurality of different materials.

For example, the hole transport region HTR may have the structure of a single layer such as a hole injection layer HIL and a hole transport layer HTL, or may have a structure of a single layer formed using a hole injection material and a hole transport material. In addition, the hole transport region HTR may have a structure of a single layer formed using a plurality of different materials, or a structure laminated one by one from the first electrode EL1 of hole injection layer HIL/hole transport layer HTL, hole injection layer HIL/hole transport layer HTL/hole buffer layer, hole injection layer HIL/hole buffer layer, hole transport layer HTL/hole buffer layer, or hole injection layer HIL/hole transport layer HTL/electron blocking layer, without limitation.

The hole transport region HTR may be formed using various suitable methods such as a vacuum deposition method, a spin coating method, a cast method, a Langmuir-Blodgett (LB) method, an inkjet printing method, a laser printing method, and a laser induced thermal imaging (LITI) method.

The hole transport region HTR may include the above-described compound including nitrogen according to an embodiment of the present disclosure. For example, the hole transport region HTR may include a compound including nitrogen, represented by Formula 1 below. The hole transport region HTR may include one or two or more kinds of the compounds including nitrogen, represented by the following Formula 1:

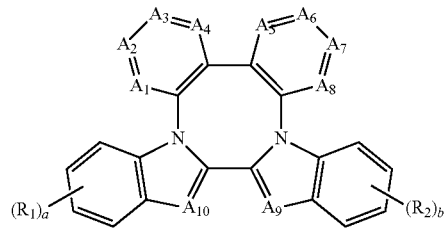

Formula 1

In Formula 1, the definitions $A_1$ to $A_{10}$, $R_1$, $R_2$, "a" and "b" are the same as described above.

For example, the hole transport region HTR may have a multilayer structure, and a layer making contact with an emission layer EML among the multilayer structure may include the compound including nitrogen according to an embodiment of the present disclosure. For example, the hole transport region HTR may include a structure laminated one by one from the first electrode EL1 of hole injection layer HIL/hole transport layer HTL/electron blocking layer EBL, and the electron blocking layer EBL may include the above-described compound including nitrogen according to an embodiment of the present disclosure.

The hole injection layer HIL may include, for example, a phthalocyanine compound such as copper phthalocyanine; N,N'-diphenyl-N,N'-bis-[4-(phenyl-m-tolyl-amino)-phenyl]-biphenyl-4,4'-diamine (DNTPD), 4,4',4"-tris(3-methylphenylphenylamino) triphenylamine (m-MTDATA), 4,4',4"-tris(N,N-diphenylamino)triphenylamine (TDATA), 4,4',4"-tris{N-(2-naphthyl)-N-phenylamino}-triphenylamine (2-TNATA), poly(3,4-ethylenedioxythiophene)/poly(4-styrenesulfonate) (PEDOT/PSS), polyaniline/dodecylbenzenesulfonic acid (PANI/DBSA), polyaniline/camphor sulfonic acid (PANI/CSA), polyaniline/poly(4-styrenesulfonate) (PANI/PSS), N,N'-dinaphthalene-1-yl)-N,N'-diphenyl-benzidine (NPD), triphenylamine-containing polyether ketone (TPAPEK), 4-isopropyl-4'-methyldiphenyliodonium tetrakis(pentafluorophenyl)borate, dipyrazino[2,3-f:2',3'-h] quinoxaline-2,3,6,7,10,11-hexacarbonitrile (HAT-CN), etc.

The hole transport layer HTL may include, for example, carbazole derivatives such as N-phenyl carbazole and polyvinyl carbazole, fluorine-based derivatives, N,N'-bis(3-methylphenyl)-N,N'-diphenyl-[1,1-biphenyl]-4,4'-diamine (TPD), triphenylamine-based derivatives such as 4,4',4"-tris (N-carbazolyl)triphenylamine (TCTA), N,N'-di(1-naphthalene-1-yl)-N,N'-diphenyl-benzidine (NPD), 4,4'-cyclohexylidene bis[N,N-bis(4-methylphenyl)benzenamine] (TAPC), 4,4'-bis[N,N'-(3-tolyl)amino]-3,3'-dimethylbiphenyl (HMTPD), etc.

The electron blocking layer EBL may include any suitable material available in the art. The electron blocking layer EBL may include, for example, carbazole derivatives such as N-phenylcarbazole, and polyvinyl carbazole, fluorine-based derivatives, N,N'-bis(3-methylphenyl)-N,N'-diphenyl-[1,1-biphenyl]-4,4'-diamine (TPD), triphenylamine-based derivatives such as 4,4',4"-tris(N-carbazolyl) triphenylamine (TCTA), N,N'-di(naphthalene-1-yl)-N,N'-diphenyl-benzidine (NPD), 4,4'-cyclohexylidene bis[N,N-bis(4-methylphenyl)benzenamine] (TAPC), 4,4'-bis[N,N'-(3-tolyl)amino]-3,3'-dimethylbiphenyl (HMTPD), mCP, etc. In addition, as described above, the electron blocking layer EBL may include the compound including nitrogen according to an embodiment of the present disclosure.

The thickness of the hole transport region HTR may be from about 100 Å to about 10,000 Å, for example, from about 100 Å to about 5,000 Å. The thickness of the hole injection layer HIL may be, for example, from about 30 Å to about 1,000 Å, and the thickness of the hole transport layer HTL may be from about 30 Å to about 1,000 Å. For example, the thickness of the electron blocking layer EBL may be from about 10 Å to about 1,000 Å. If the case the thicknesses of the hole transport region HTR, the hole injection layer HIL, the hole transport layer HTL, and the electron blocking layer EBL satisfy the above-described ranges, satisfactory or suitable hole transport properties may be obtained without substantial increase of a driving voltage.

The hole transport region HTR may further include a charge generating material other than the above-described materials to improve conductivity. The charge generating material may be dispersed in the hole transport region HTR uniformly or non-uniformly. The charge generating material may be, for example, a p-dopant. The p-dopant may be one of quinone derivatives, metal oxides, or cyano group-containing compounds, without limitation. For example, non-limiting examples of the p-dopant may include quinone derivatives such as tetracyanoquinodimethane (TCNQ) and 2,3,5,6-tetrafluoro-tetracyanoquinodimethane (F4-TCNQ), metal oxides such as tungsten oxide, and molybdenum oxide, without limitation.

As described above, the hole transport region HTR may further include at least one of a hole buffer layer or an electron blocking layer. The hole buffer layer may compensate a resonance distance according to the wavelength of light emitted from the emission layer EML and increase light emission efficiency. Materials included in the hole transport region HTR may be used as materials included in the hole buffer layer. The electron blocking layer is a layer that prevents or reduces electron injection from the electron transport region ETR to the hole transport region HTR.

The emission layer EML is provided on the hole transport region HTR. The thickness of the emission layer EML may be, for example, from about 100 Å to about 1,000 Å, or from about 100 Å to about 300 Å. The emission layer EML may have a single layer formed using a single material, a single layer formed using a plurality of different materials, or a multilayer structure having a plurality of layers formed using a plurality of different materials.

The emission layer EML may include the above-described compound including nitrogen according to an embodiment of the present disclosure. The above-described compound including nitrogen according to an embodiment of the present disclosure may be included in at least one of the hole transport region HTR or the emission layer EML.

The emission layer EML may include one or two or more kinds of the compounds including nitrogen, represented by Formula 1. The emission layer EML may further include any suitable material available in the art in addition to the compound including nitrogen, represented by Formula 1. For example, a fluorescent material including any one selected from the group consisting of spiro-DPVBi, 2,2',7, 7'-tetrakis(biphenyl-4-yl)-9,9'-spirobifluorene (spiro-6P, spiro-sexiphenyl), distyryl-benzene (DSB), distyryl-arylene (DSA), a polyfluorene (PFO)-based polymer, and a poly(p-phenylene vinylene) (PPV)-based polymer may be further included. However, an embodiment of the present disclosure is not limited thereto.

The emission layer may be an emission layer emitting thermally activated delayed fluorescence. For example, the emission layer may be a blue emission layer emitting blue light via thermally activated delayed fluorescence.

The emission layer EML may include a host and a dopant, and the host may include the compound including nitrogen according to an embodiment of the present disclosure. However, an embodiment of the present disclosure is not limited thereto. The host may include any suitable material available in the art. For example, tris(8-hydroxyquinolino) aluminum ($Alq_3$), 4,4'-bis(N-carbazolyl)-1,1'-biphenyl (CBP), poly(n-vinylcarbazole) (PVK), 9,10-di(naphthalene-2-yl)anthracene (ADN), 4,4',4''-tris(carbazol-9-yl)-triphenylamine (TCTA), 1,3,5-tris(N-phenylbenzimidazole-2-yl)benzene (TPBi), 3-tert-butyl-9,10-di(naphth-2-yl)anthracene (TBADN), distyrylarylene (DSA), 4,4'-bis(9-carbazolyl)-2,2'-dimethyl-biphenyl (CDBP), 2-methyl-9,10-bis(naphthalen-2-yl)anthracene (MADN), bis[2-(diphenylphosphino)phenyl] ether oxide (DPEPO), hexaphenyl cyclotriphosphazene (CP1), 1,4-bis(triphenylsilyl)benzene (UGH2), hexaphenylcyclotrisiloxane ($DPSiO_3$), octaphenylcyclotetra siloxane ($DPSiO_4$), 2,8-bis(diphenylphosphoryl)dibenzofuran (PPF), etc. may be used.

The dopant may employ any suitable material available in the art, without limitation. The dopant may include a fluorescent dopant or a phosphorescent dopant. The dopant may include a thermally activated delayed fluorescent dopant, for example, 10-phenyl-10H,10'H-spiro[acridine-9,9'-anthracene]-10'-one (ACRSA), 3,4,5,6-tetra-9H-carbazole-9-yl-1, 2-benzenedicarbonitrile (4CzPN), 2,4,5,6-tetra-9H-carbazole-9-yl-isophthalonitrile (4CzIPN), bis[4-9,9-dimethyl-9, 10-dihydroacridine]phenyl]sulfone (DMAC-DPS), or 2-phenoxazine-4,6-diphenyl-1,3,5-triazine (PSZ-TRZ).

The electron transport region ETR is provided on the emission layer EML. The electron transport region ETR may include at least one of a hole blocking layer, an electron transport layer ETL, or an electron injection layer EIL, without limitation.

The electron transport region ETR may have a single layer formed using a single material, a single layer formed using a plurality of different materials, or a multilayer structure including a plurality of layers formed using a plurality of different materials.

For example, the electron transport region ETR may have the structure of a single layer such as an electron injection layer EIL and an electron transport layer ETL, or a single layer structure formed using an electron injection material and an electron transport material. In addition, the electron transport region ETR may have a single layer structure formed using a plurality of different materials, or a structure laminated one by one from the emission layer EML of electron transport layer ETL/electron injection layer EIL, or hole blocking layer/electron transport layer ETL/electron injection layer EIL, without limitation. The thickness of the electron transport region ETR may be, for example, from about 1,000 Å to about 1,500 Å.

The electron transport region ETR may be formed using various suitable methods such as a vacuum deposition method, a spin coating method, a cast method, a Langmuir-Blodgett (LB) method, an inkjet printing method, a laser printing method, and a laser induced thermal imaging (LITI) method.

If the electron transport region ETR includes the electron transport layer ETL, the electron transport region ETR may include tris(8-hydroxyquinolinato)aluminum ($Alq_3$), 1,3,5-tri[(3-pyridyl)-phen-3-yl]benzene, 2,4,6-tris(3'-(pyridin-3-yl)biphenyl-3-yl)-1,3,5-triazine, bis[2-(diphenylphosphino) phenyl]ether oxide (DPEPO), 2-(4-(N-phenylbenzoimidazolyl-1-ylphenyl)-9,10-dinaphthylanthracene, 1,3,5-tri(1-phenyl-1H-benzo[d]imidazol-2-yl)phenyl (TPBi), 2,9-dimethyl-4,7-diphenyl-1, 10-phenanthroline (BCP), 4,7-diphenyl-1,10-phenanthroline (Bphen), 3-(4-biphenylyl)-4-phenyl-5-tert-butylphenyl-1,2,4-triazole (TAZ), 4-(naphthalen-1-yl)-3,5-diphenyl-4H-1,2,4-triazole (NTAZ), 2-(4-biphenylyl)-5-(4-tert-butylphenyl)-1,3,4-oxadiazole (tBu-PBD), bis(2-methyl-8-quinolinolato-N1,O8)-(1,1'-biphenyl-4-olato) aluminum (BAlq), berylliumbis(benzoquinolin-10-olate (Bebq$_2$), 9,10-di(naphthalene-2-yl)anthracene (ADN), or a mixture thereof, without limitation. The thickness of the electron transport layer ETL may be from about 100 Å to about 1,000 Å, for example, from about 150 Å to about 500 Å. If the thickness of the electron transport layer ETL satisfies the above-described range, satisfactory or suitable electron transport properties may be obtained without the substantial increase of a driving voltage.

If the electron transport region ETR includes the electron injection layer EIL, the electron transport region ETR may include LiF, lithium quinolate (LiQ), Li$_2$O, BaO, NaCl, CsF, a metal in lanthanides such as Yb, or a metal halide such as RbCl and Rbl, without limitation. The electron injection layer EIL also may be formed using a mixture material of an electron transport material and an insulating organo metal salt. The organo metal salt may be a material having an energy band gap of about 4 eV or more. For example, the organo metal salt may include, for example, a metal acetate, a metal benzoate, a metal acetoacetate, a metal acetylacetonate, or a metal stearate. The thickness of the electron injection layer EIL may be from about 1 Å to about 100 Å, and from about 3 Å to about 90 Å. If the thickness of the electron injection layer EIL satisfies the above described range, satisfactory or suitable electron injection properties may be obtained without inducing the substantial increase of a driving voltage.

The electron transport region ETR may include a hole blocking layer, as described above. The hole blocking layer may include, for example, 2,9-dimethyl-4,7-diphenyl-1,10-phenanthroline (BCP), 4,7-diphenyl-1,10-phenanthroline (Bphen), bis[2-(diphenylphosphino)phenyl]ether oxide (DPEPO), etc. without limitation.

The second electrode EL2 is provided on the electron transport region ETR. The second electrode EL2 may be a common electrode or a cathode. The second electrode EL2 may be a transmissive electrode, a transflective electrode or a reflective electrode. If the second electrode EL2 is the transmissive electrode, the second electrode EL2 may include a transparent metal oxide, for example, ITO, IZO, ZnO, ITZO, etc.

If the second electrode EL2 is the transflective electrode or reflective electrode, the second electrode EL2 may include Ag, Mg, Cu, Al, Pt, Pd, Au, Ni, Nd, Ir, Cr, Li, Ca, LiF/Ca, LiF/Al, Mo, Ti, a compound thereof, or a mixture thereof (for example, a mixture of Ag and Mg). Also, the second electrode EL2 may include a plurality of layers including the reflective layer or transflective layer formed using the above materials, or a transparent layer formed using ITO, IZO, ZnO, or ITZO.

The second electrode EL2 may be coupled or connected with an auxiliary electrode. If the second electrode EL2 is coupled or connected with the auxiliary electrode, the resistance of the second electrode EL2 may be decreased.

In the organic electroluminescence device 10, voltages are applied to each of the first electrode EL1 and the second electrode EL2, and holes injected move from the first electrode EL1 via the hole transport region HTR to the emission layer EML, and electrons injected move from the second electrode EL2 via the electron transport region ETR to the emission layer EML. The electrons and holes are recombined in the emission layer EML to generate excitons, and the excitons may emit light via transition from an excited state to a ground state.

If the organic electroluminescence device 10 is a top emission type (or kind), the first electrode EL1 may be a reflective electrode, and the second electrode EL2 may be a transmissive electrode or a transflective electrode. If the organic electroluminescence device 10 is a bottom emission type (or kind), the first electrode EL1 may be the transmissive electrode or the transflective electrode, and the second electrode EL2 may be the reflective electrode.

The organic electroluminescence device 10 according to an embodiment of the present disclosure is characterized in including the compound including nitrogen, represented by Formula 1 which has a relatively high triplet energy level, and may achieve high efficiency.

Hereinafter, the subject matter of the present disclosure will be explained in more detail referring to embodiments and comparative embodiments. The following embodiments are only for illustration to assist the understanding of the present disclosure, and the scope of the present disclosure is not limited thereto.

Synthetic Examples

The compound including nitrogen according to an embodiment of the present disclosure may be synthesized, for example, as follows. However, the synthetic method of the compound including nitrogen according to an embodiment of the present disclosure is not limited thereto.

1. Synthesis of Compound 2

Compound 2 which is a compound including nitrogen according to an embodiment of the present disclosure may be synthesized, for example, by the following reaction:

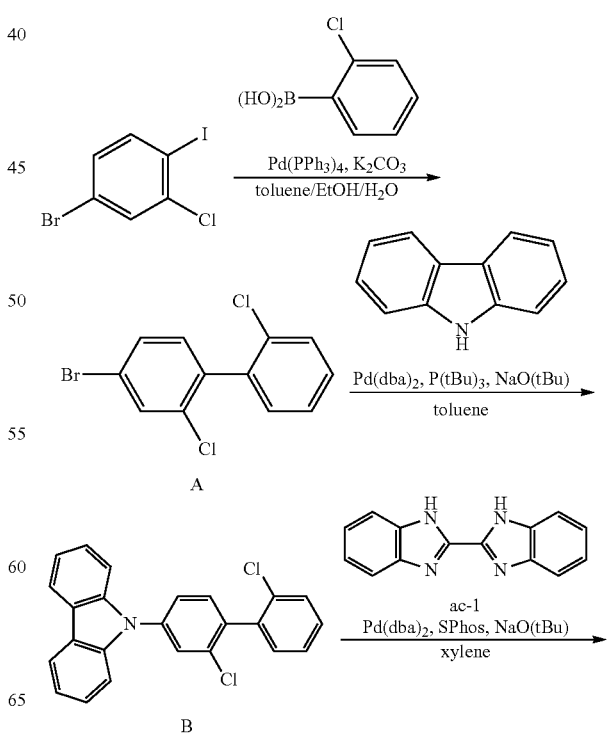

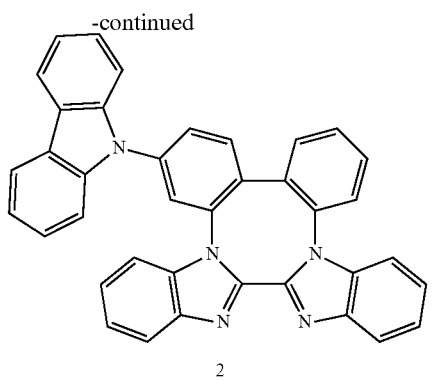

2

(Synthesis of Compound A)

Under an argon (Ar) atmosphere, 4-bromo-2-chloro-1-iodobenzene (5.00 g), (2-chlorophenyl)boronic acid (2.46 g), tetrakis(triphenylphosphine)palladium(0) (Pd(PPh$_3$)$_4$, 0.91 g), and potassium carbonate (K$_2$CO$_3$, 4.35 g) were dissolved in a mixture solvent of degassed toluene/ethanol/water (10:1:2, 200 ml) in a 500 ml three-neck flask, followed by stirring at about 80° C. for about 16 hours. After the reaction, water was added and extraction with toluene was conducted. Organic layers were collected and dried with MgSO$_4$. Solvents were removed under a reduced pressure. The crude product thus obtained was separated by silica gel column chromatography to obtain 3.47 g (yield 73%) of Compound A. The molecular weight of Compound A measured by fast atom bombardment-mass spectrometry (FAB-MS) was 301.

(Synthesis of Compound B)

Under an argon (Ar) atmosphere, Compound A (3.00 g), carbazole (1.66 g), bis(dibenzylideneacetone)palladium(0) (Pd(dba)$_2$, 0.29 g), tri-tert-butylphosphine (P(tBu)$_3$, 0.40 g), and sodium tert-butoxide (NaO(tBu), 0.96 g) were dissolved in anhydrous toluene (200 ml) in a 500 ml three-neck flask, followed by heating and refluxing for about 8 hours. After the reaction, water was added and extraction with toluene was conducted. Organic layers were collected and dried with MgSO$_4$. Solvents were removed under a reduced pressure. The crude product thus obtained was separated by silica gel column chromatography to obtain 3.32 g (yield 86%) of Compound B. The molecular weight of Compound B measured by FAB-MS was 388.

(Synthesis of Compound Ac-1)

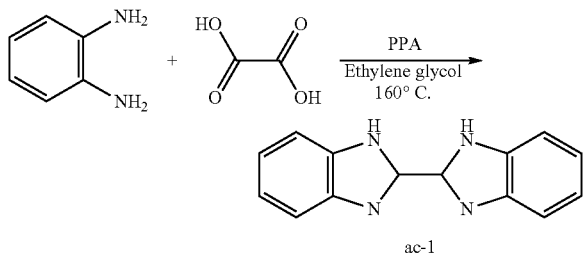

ac-1

Compound ac-1 which corresponded to 1H,1'H-2,2'-bibenz[d]imidazole was synthesized referring to Bioorg. Med. Chem. 24 (2016) 5103-5114, the entire content of which is incorporated herein by reference.

(Synthesis of Compound 2)

Under an argon (Ar) atmosphere, Compound B (3.00 g), Compound ac-1 (1.81 g), Pd(dba)$_2$ (0.89 g), 2-dicyclohexylphosphino-2',6'-dimethoxybiphenyl (Sphos, 1.27 g), and NaO(tBu) (1.50 g) were dissolved in anhydrous xylene (200 ml) in a 500 ml three-neck flask, followed by heating and refluxing for about 6 hours. After the reaction, water was added and extraction with CH$_2$Cl$_2$ was conducted. Organic layers were collected and dried with MgSO$_4$. Solvents were removed under a reduced pressure. The crude product thus obtained was separated by silica gel column chromatography to obtain 1.02 g (yield 24%) of Compound 2. The molecular weight of Compound 2 measured by FAB-MS was 549.

2. Synthesis of Compound 7

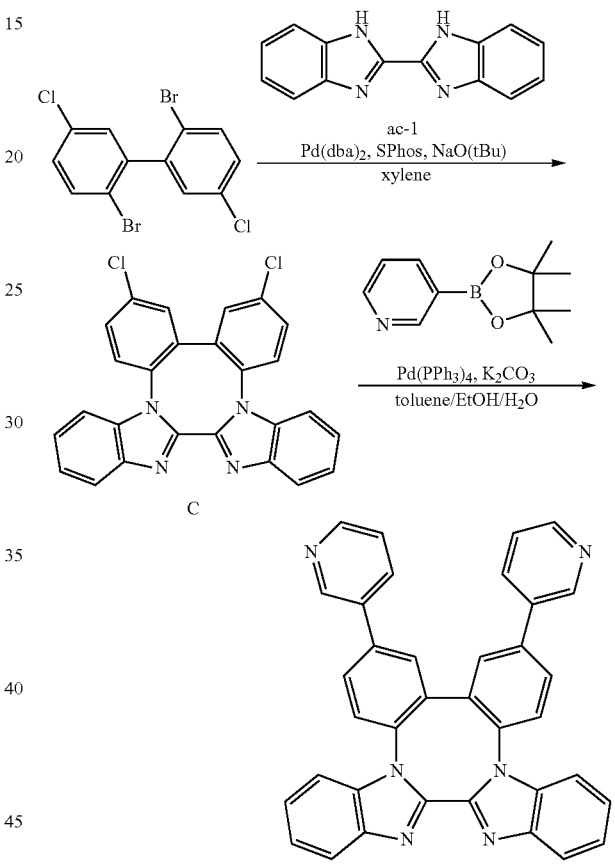

(Synthesis of Compound C)

Under an argon (Ar) atmosphere, 2,2'-dibromo-5,5'-dichloro-1,1'-biphenyl (3.00 g), Compound ac-1 (1.84 g), Pd(dba)$_2$ (0.91 g), SPhos (1.29 g), and NaO(tBu) (1.51 g) were dissolved in anhydrous xylene (200 ml) in a 500 ml three-neck flask, followed by heating and refluxing for about 6 hours. After the reaction, water was added and extraction with CH$_2$Cl$_2$ was conducted. Organic layers were collected and dried with MgSO$_4$. Solvents were removed under a reduced pressure. The crude product thus obtained was separated by silica gel column chromatography to obtain 1.18 g (yield 33%) of Compound C. The molecular weight of Compound C measured by FAB-MS was 453.

(Synthesis of Compound 7)

Under an argon (Ar) atmosphere, Compound C (1.00 g), 3-(4,4,5,5-tetramethyl-1,3,2-dioxaborolan-2-yl)pyridine (1.00 g), Pd(PPh$_3$)$_4$ (0.50 g), and K$_2$CO$_3$ (1.52 g) were dissolved in a mixture solvent of degassed toluene/ethanol/ water (10:1:2, 50 ml) in a 500 ml three-neck flask, followed by stirring at about 80° C. for about 16 hours. After the reaction, water was added and extraction with $CH_2Cl_2$ was conducted. Organic layers were collected and dried with $MgSO_4$. Solvents were removed under a reduced pressure. The crude product thus obtained was separated by silica gel column chromatography to obtain 0.85 g (yield 80%) of Compound 7. The molecular weight of Compound 7 measured by FAB-MS was 538.

3. Synthesis of Compound 14

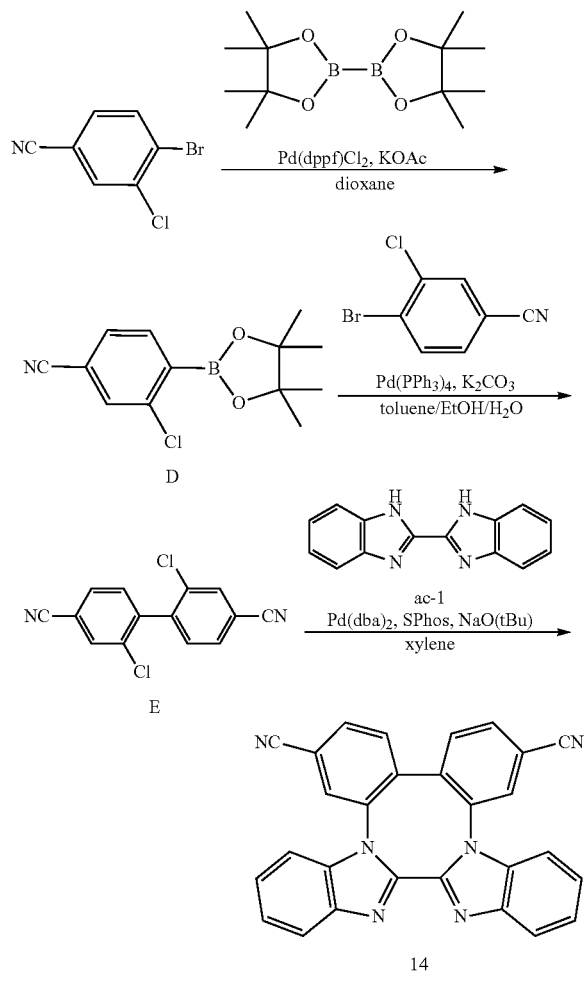

(Synthesis of Compound D)

Under an argon (Ar) atmosphere, 4-bromo-3-chlorobenzonitrile (3.00 g), bis(pinacolato)diboron (5.27 g), [1,1;-bis(diphenylphosphino)ferrocene]dichloropalladium(II) dichloromethane adduct (Pd(pddf)$Cl_2$, 1.13 g), and potassium acetate (KOAc, 4.08 g) were dissolved in anhydrous 1,4-dioxane (100 ml) in a 500 ml three-neck flask, followed by stirring at about 100° C. for about 8 hours. After the reaction, water was added and extraction with $CH_2Cl_2$ was conducted. Organic layers were collected and dried with $MgSO_4$. Solvents were removed under a reduced pressure. The crude product thus obtained was separated by silica gel column chromatography to obtain 2.92 g (yield 80%) of Compound D. The molecular weight of Compound D measured by FAB-MS was 263.

(Synthesis of Compound E)

Under an argon (Ar) atmosphere, Compound D (2.50 g), 4-bromo-3-chlorobenzonitrile (2.05 g), Pd(PPh$_3$)$_4$ (1.09 g), and $K_2CO_3$ (2.62 g) were dissolved in a mixture solvent of degassed toluene/ethanol/water (10:1:2, 100 ml) in a 500 ml three-neck flask, followed by stirring at about 80° C. for about 16 hours. After the reaction, water was added and extraction with $CH_2Cl_2$ was conducted. Organic layers were collected and dried with $MgSO_4$. Solvents were removed under a reduced pressure. The crude product thus obtained was separated by silica gel column chromatography to obtain 1.94 g (yield 75%) of Compound E. The molecular weight of Compound E measured by FAB-MS was 273.

(Synthesis of Compound 14)

Under an argon (Ar) atmosphere, Compound E (1.90 g), Compound ac-1 (1.62 g), Pd(dba)$_2$ (0.80 g), SPhos (1.14 g), and NaO(tBu) (1.34 g) were dissolved in anhydrous xylene (200 ml) in a 500 ml three-neck flask, followed by heating and refluxing for about 6 hours. After the reaction, water was added and extraction with $CH_2Cl_2$ was conducted. Organic layers were collected and dried with $MgSO_4$. Solvents were removed under a reduced pressure. The crude product thus obtained was separated by silica gel column chromatography to obtain 0.97 g (yield 32%) of Compound 14. The molecular weight of Compound 14 measured by FAB-MS was 434.

4. Synthesis of Compound 15

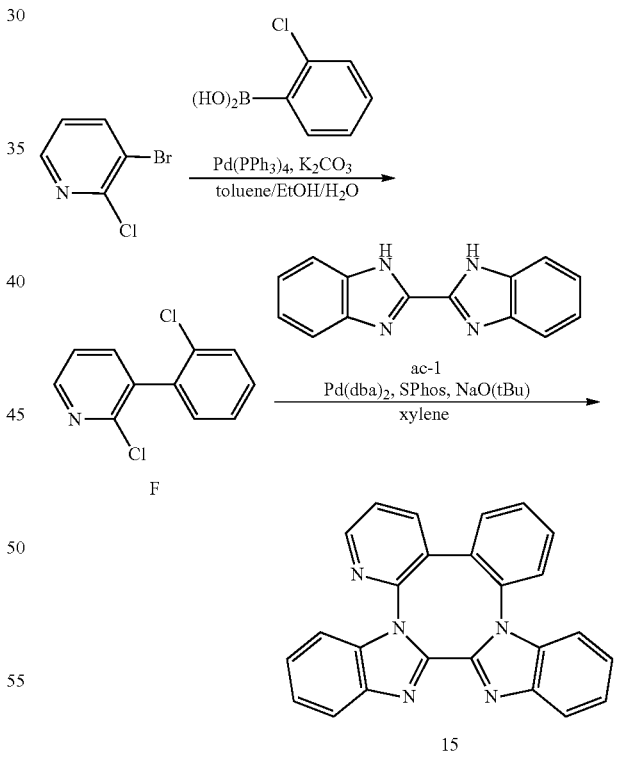

(Synthesis of Compound F)

Under an argon (Ar) atmosphere, 3-bromo-2-chloropyridine (5.00 g), (2-chlorophenyl)boronic acid (4.06 g), Pd(PPh$_3$)$_4$, (1.50 g) and $K_2CO_3$ (7.12 g) were dissolved in a mixture solvent of degassed toluene/ethanol/water (10:1:2, 130 ml) in a 500 ml three-neck flask, followed by stirring at about 80° C. for about 16 hours. After the reaction, water was added and extraction with $CH_2Cl_2$ was conducted.

Organic layers were collected and dried with MgSO$_4$. Solvents were removed under a reduced pressure. The crude product thus obtained was separated by silica gel column chromatography to obtain 4.08 g (yield 70%) of Compound F. The molecular weight of Compound F measured by FAB-MS was 224.

(Synthesis of Compound 15)

Under an argon (Ar) atmosphere, Compound F (4.00 g), Compound ac-1 (4.18 g), Pd(dba)$_2$ (2.05 g), SPhos (2.93 g), and NaO(tBu) (3.43 g) were dissolved in anhydrous xylene (100 ml) in a 500 ml three-neck flask, followed by heating and refluxing for about 8 hours. After the reaction, water was added and extraction with CH$_2$Cl$_2$ was conducted. Organic layers were collected and dried with MgSO$_4$. Solvents were removed under a reduced pressure. The crude product thus obtained was separated by silica gel column chromatography to obtain 1.31 g (yield 19%) of Compound 15. The molecular weight of Compound 15 measured by FAB-MS was 385.

5. Synthesis of Compound 18

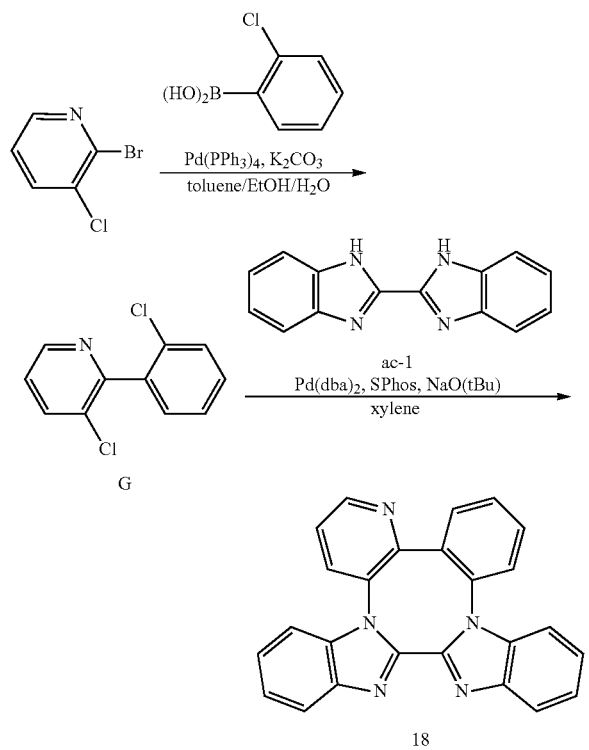

(Synthesis of Compound G)

Under an argon (Ar) atmosphere, 2-bromo-3-chloropyridine (5.00 g), (2-chlorophenyl)boronic acid (4.07 g), Pd(PPh$_3$)$_4$, (1.50 g) and K$_2$CO$_3$ (7.15 g) were dissolved in a mixture solvent of degassed toluene/ethanol/water (10:1:2, 130 ml) in a 500 ml three-neck flask, followed by stirring at about 80° C. for about 16 hours. After the reaction, water was added and extraction with CH$_2$Cl$_2$ was conducted. Organic layers were collected and dried with MgSO$_4$. Solvents were removed under a reduced pressure. The crude product thus obtained was separated by silica gel column chromatography to obtain 4.19 g (yield 72%) of Compound G. The molecular weight of Compound G measured by FAB-MS was 224.

(Synthesis of Compound 18)

Under an argon (Ar) atmosphere, Compound G (4.00 g), Compound ac-1 (4.18 g), Pd(dba)$_2$ (2.06 g), SPhos (2.92 g), and NaO(tBu) (3.45 g) were dissolved in anhydrous xylene (100 ml) in a 500 ml three-neck flask, followed by heating and refluxing for about 8 hours. After the reaction, water was added and extraction with CH$_2$Cl$_2$ was conducted. Organic layers were collected and dried with MgSO$_4$. Solvents were removed under a reduced pressure. The crude product thus obtained was separated by silica gel column chromatography to obtain 1.17 g (yield 17%) of Compound 18. The molecular weight of Compound 18 measured by FAB-MS was 385.

6. Synthesis of Compound 25

(Synthesis of Compound H)

Under an argon (Ar) atmosphere, 5-bromo-4-chloro-2-phenylpyrimidine (5.00 g), (2-chlorophenyl)boronic acid (2.90 g), Pd(PPh$_3$)$_4$, (1.07 g) and K$_2$CO$_3$ (5.13 g) were dissolved in a mixture solvent of degassed toluene/ethanol/water (10:1:2, 100 ml) in a 500 ml three-neck flask, followed by stirring at about 80° C. for about 16 hours. After the reaction, water was added and extraction with CH$_2$Cl$_2$ was conducted. Organic layers were collected and dried with MgSO$_4$. Solvents were removed under a reduced pressure. The crude product thus obtained was separated by silica gel column chromatography to obtain 4.25 g (yield 76%) of Compound F. The molecular weight of Compound F measured by FAB-MS was 301.

(Synthesis of Compound 25)

Under an argon (Ar) atmosphere, Compound F (4.00 g), Compound ac-1 (3.11 g), Pd(dba)$_2$ (1.53 g), SPhos (2.18 g), and NaO(tBu) (2.55 g) were dissolved in anhydrous xylene (200 ml) in a 500 ml three-neck flask, followed by heating and refluxing for about 6 hours. After the reaction, water was added and extraction with CH$_2$Cl$_2$ was conducted. Organic layers were collected and dried with MgSO$_4$. Solvents were removed under a reduced pressure. The crude product thus obtained was separated by silica gel column chromatography to obtain 1.23 g (yield 20%) of Compound 25. The molecular weight of Compound 25 measured by FAB-MS was 462.

7. Synthesis of Compound 26

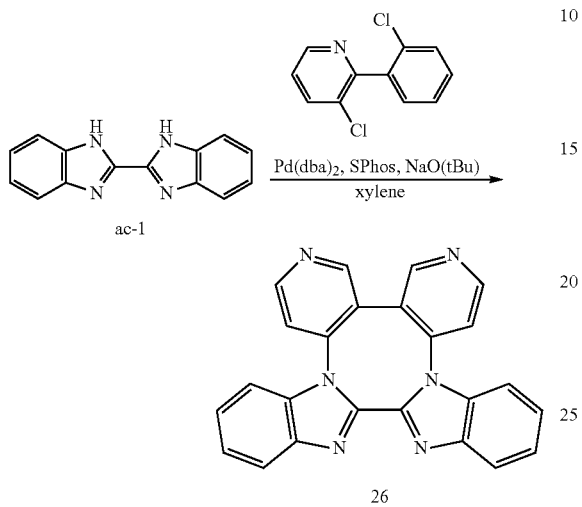

Under an argon (Ar) atmosphere, Compound ac-1 (5.00 g), 4,4'-dichloro-3,3'-bipyridine (4.80 g), Pd(dba)$_2$ (2.46 g), SPhos (3.50 g), and NaO(tBu) (4.10 g) were dissolved in anhydrous xylene (100 ml) in a 500 ml three-neck flask, followed by heating and refluxing for about 6 hours. After the reaction, water was added and extraction with CH$_2$Cl$_2$ was conducted. Organic layers were collected and dried with MgSO$_4$. Solvents were removed under a reduced pressure. The crude product thus obtained was separated by silica gel column chromatography to obtain 1.73 g (yield 21%) of Compound 26. The molecular weight of Compound 26 measured by FAB-MS was 386.

8. Synthesis of Compound 27

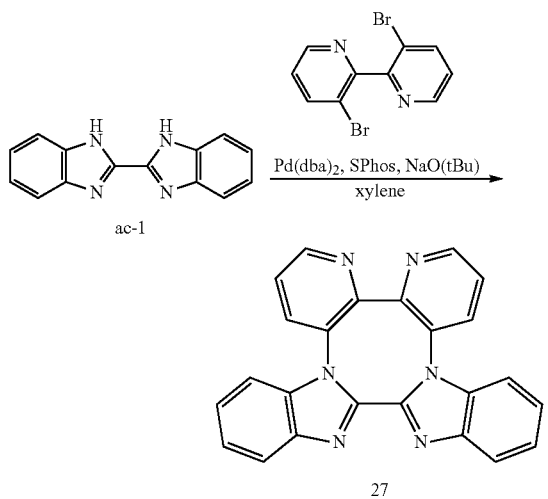

Under an argon (Ar) atmosphere, Compound ac-1 (5.00 g), 3,3'-dibromo-2,2'-bipyridine (6.70 g), Pd(dba)$_2$ (2.44 g), SPhos (3.50 g; 2-Dicyclohexylphosphino-2',6'-dimethoxybiphenyl), and NaO(tBu) (4.15 g) were dissolved in anhydrous xylene (100 ml) in a 500 ml three-neck flask, followed by heating and refluxing for about 6 hours. After the reaction, water was added and extraction with CH$_2$Cl$_2$ was conducted. Organic layers were collected and dried with MgSO$_4$. Solvents were removed under a reduced pressure. The crude product thus obtained was separated by silica gel column chromatography to obtain 1.32 g (yield 16%) of Compound 27. The molecular weight of Compound 27 measured by FAB-MS was 386.

9. Synthesis of Compound 48
(Synthesis of Compound Ac-2)

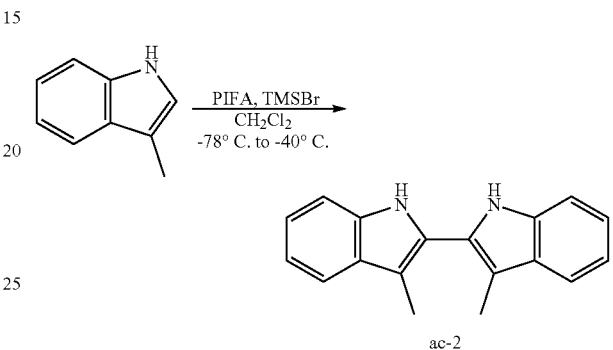

Compound ac-2 which corresponded to 3,3'-dimethyl-1H,1'H-2,2'-biindole was synthesized referring to Tetrahedron 65 (2009) 10797-10815, the entire content of which is incorporated herein by reference.

(Synthesis of Compound 48)

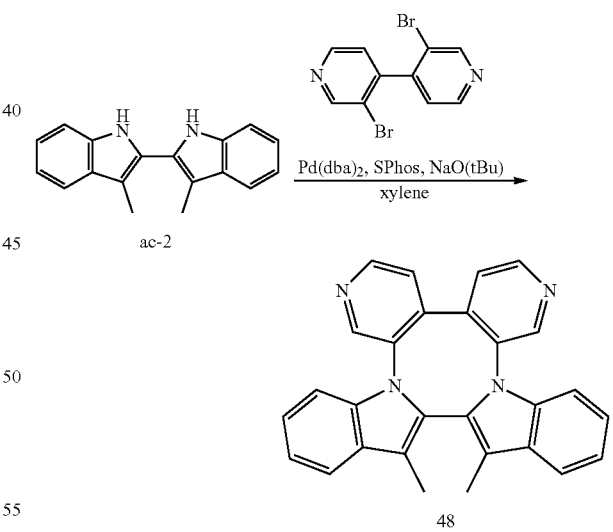

Under an argon (Ar) atmosphere, Compound ac-2 (5.00 g), 3,3'-dibromo-4,4'-bipyridine (6.03 g), Pd(dba)$_2$ (2.20 g), SPhos (3.15 g), and NaO(tBu) (3.69 g) were dissolved in anhydrous xylene (220 ml) in a 500 ml three-neck flask, followed by heating and refluxing for about 6 hours. After the reaction, water was added and extraction with CH$_2$Cl$_2$ was conducted. Organic layers were collected and dried with MgSO$_4$. Solvents were removed under a reduced pressure. The crude product thus obtained was separated by silica gel column chromatography to obtain 1.66 g (yield 21%) of Compound 48. The molecular weight of Compound 48 measured by FAB-MS was 412.

10. Synthesis of Compound 60
(Synthesis of Compound Ac-3)

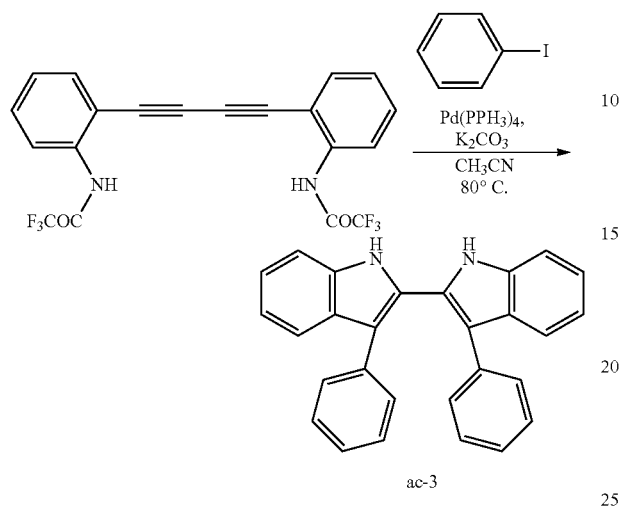

Compound ac-3 which corresponded to 3,3'-diphenyl-1H,1'H-2,2'-biindole was synthesized referring to Tetrahedron 62 (2006) 3039-3039, the entire content of which is incorporated herein by reference.

(Synthesis of Compound 60)

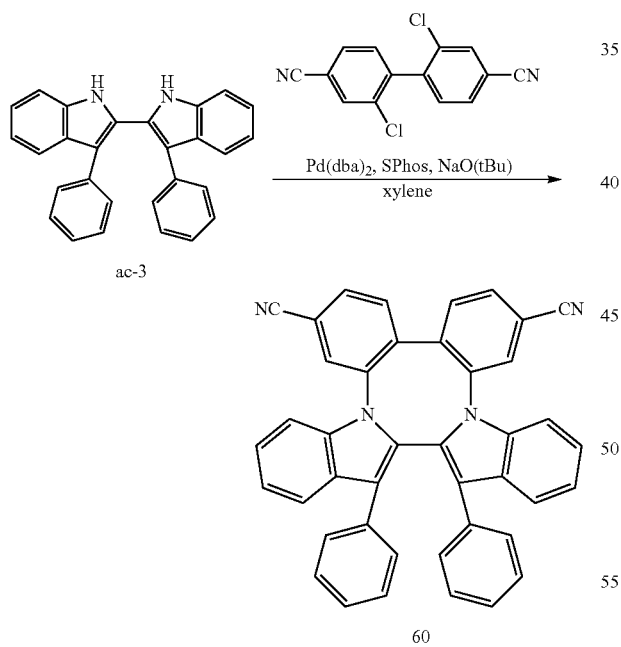

Under an argon (Ar) atmosphere, Compound ac-3 (5.00 g), Compound E (3.55 g), Pd(dba)$_2$ (1.49 g), SPhos (2.13 g), and NaO(tBu) (2.50 g) were dissolved in anhydrous xylene (70 ml) in a 500 ml three-neck flask, followed by heating and refluxing for about 6 hours. After the reaction, water was added and extraction with CH$_2$Cl$_2$ was conducted. Organic layers were collected and dried with MgSO$_4$. Solvents were removed under a reduced pressure. The crude product thus obtained was separated by silica gel column chromatography to obtain 1.44 g (yield 15%) of Compound 60. The molecular weight of Compound 60 measured by FAB-MS was 584.

(Device Manufacturing Example 1)

Organic electroluminescence devices of Examples 1 to 10 were manufactured using Compounds 2, 7, 14, 15, 18, 25, 26, 27, 48 and 60 as host materials of an emission layer.

[Example Compounds]

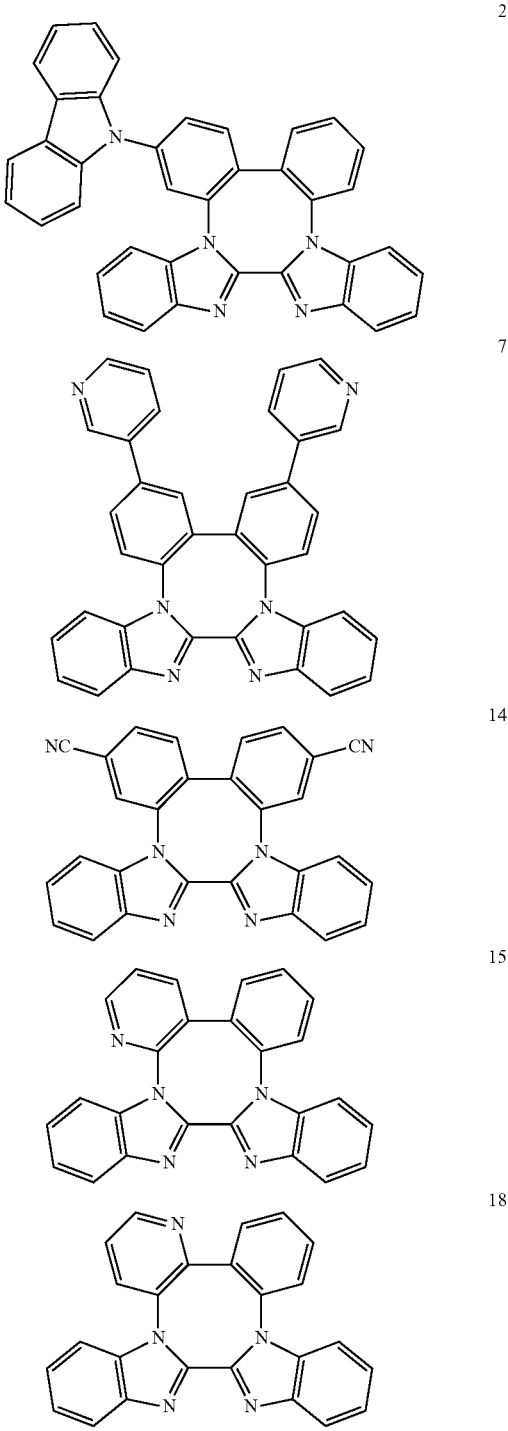

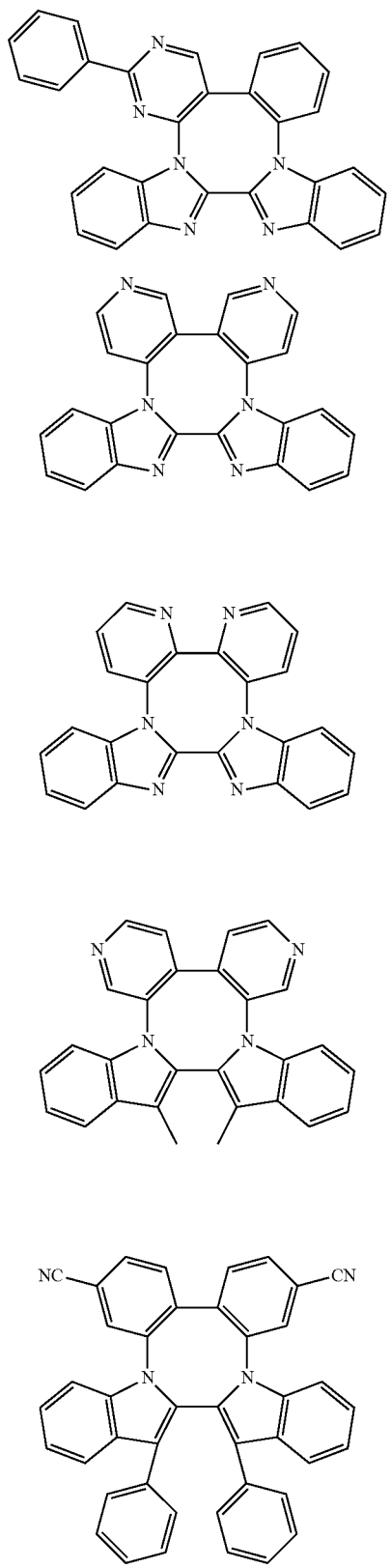
[Comparative Compounds]
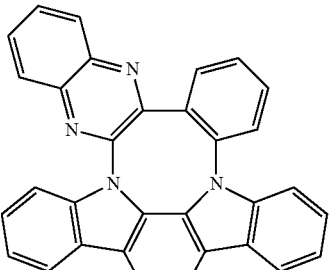
X-1
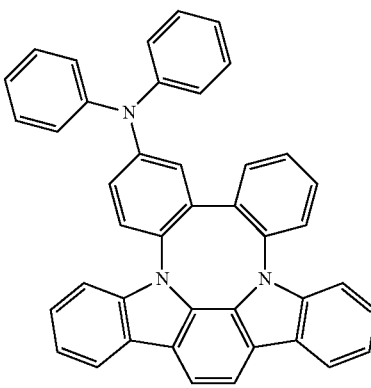
X-2
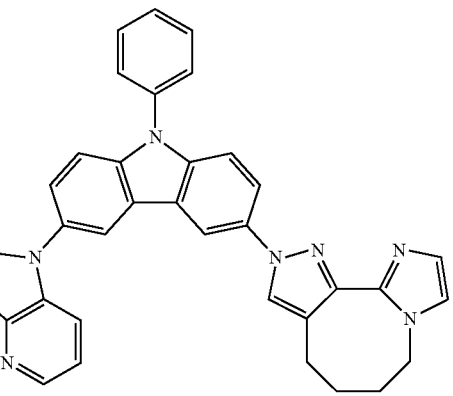
X-3
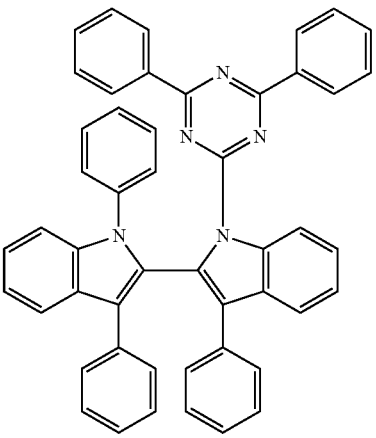
X-4
Organic electroluminescence devices of Comparative Examples 1 to 4 were manufactured using Example Compounds X-1 to X-4 as host materials of an emission layer.
The organic electroluminescence devices of Examples 1 to 10 and Comparative Examples 1 to 4 were manufactured as follows. A first electrode with a thickness of about 150 nm was formed using ITO, a hole injection layer with a thickness of about 10 nm was formed using HAT-CN, a hole transport layer with a thickness of about 80 nm was formed using α-NPD, an electron blocking layer with a thickness of about 5 nm was formed using mCP, an emission layer with a thickness of about 20 nm was formed using the example compound or the comparative compound doped with 18% ACRSA, a hole blocking layer with a thickness of about 10 nm was formed using DPEPO, an electron transport layer with a thickness of about 30 nm was formed using TPBi, an electron injection layer with a thickness of about 0.5 nm was formed using LiF, and a second electrode with a thickness of about 100 nm was formed using Al. Each layer was formed by a vacuum deposition method.

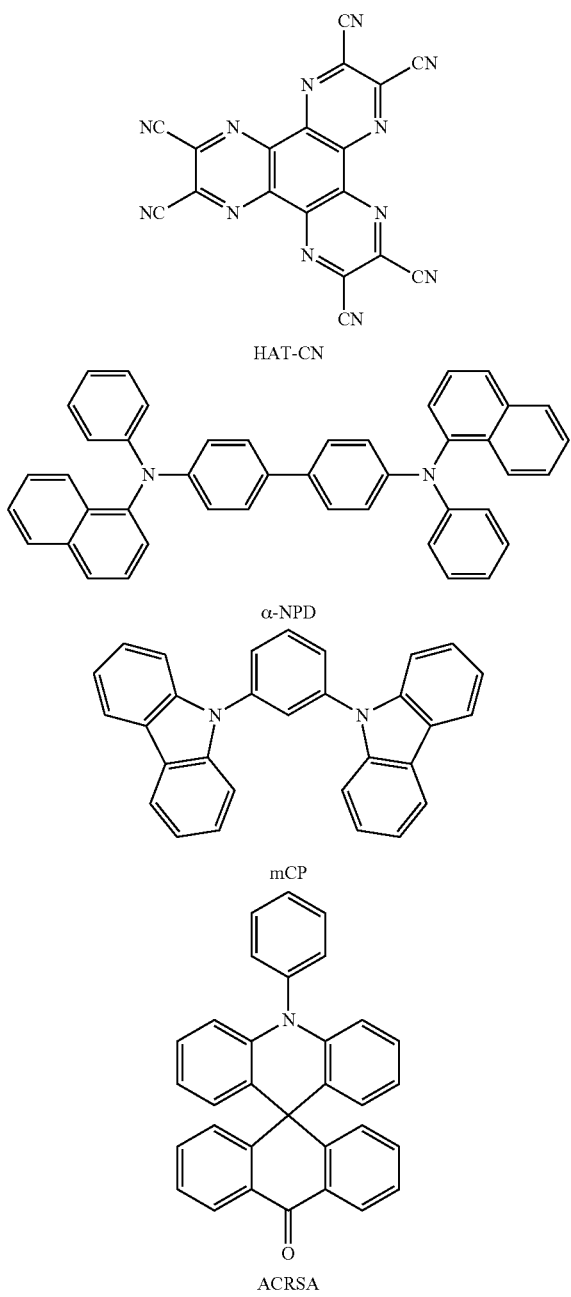

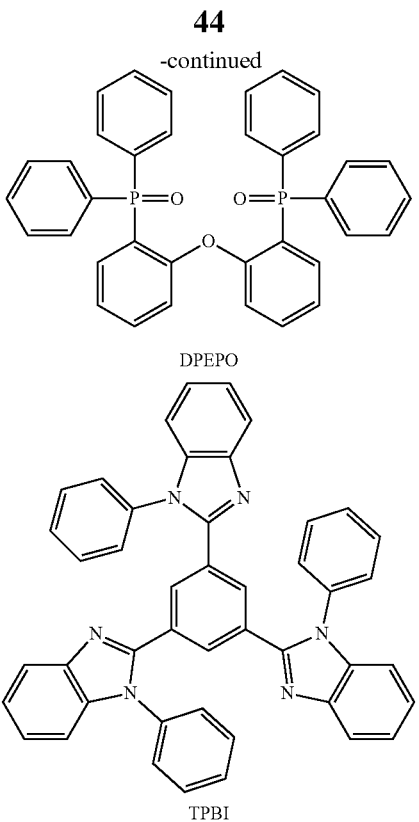

TABLE 1

| | Host of emission layer | Maximum emission efficiency |
|---|---|---|
| Example 1 | Example Compound 2 | 140% |
| Example 2 | Example Compound 7 | 170% |
| Example 3 | Example Compound 14 | 155% |
| Example 4 | Example Compound 15 | 170% |
| Example 5 | Example Compound 18 | 180% |
| Example 6 | Example Compound 25 | 150% |
| Example 7 | Example Compound 26 | 160% |
| Example 8 | Example Compound 27 | 160% |
| Example 9 | Example Compound 48 | 150% |
| Example 10 | Example Compound 60 | 130% |
| Comparative Example 1 | Comparative Compound X-1 | 100% |
| Comparative Example 2 | Comparative Compound X-2 | 90% |
| Comparative Example 3 | Comparative Compound X-3 | 90% |
| Comparative Example 4 | Comparative Compound X-4 | 100% |

Referring to Table 1, it may be found that if the compound including nitrogen according to an embodiment of the present disclosure is applied to a host material of an emission layer of an organic electroluminescence device, high efficiency may be achieved. For example, when Examples 1 to 10 are compared to Comparative Examples 1 and 2, it may be found that the efficiency was even further improved. This is achieved because the example compounds have inferior planarity to the comparative compounds and have a high triplet energy level, and energy transfer from a dopant to a host is restrained. Accordingly, efficient emission of thermally activated delayed fluorescence is available. In Comparative Example 3, an eight-member ring structure including biimidazole is included but a ring structure is formed using alkyl groups. Thus, stability is insufficient or unsuitable, and smaller efficiency than the examples is attained. When Example 10 is compared to Comparative Example 4, the example compound has an eight-member ring structure, a dihedral angle between indole groups around biindole is fixed to a twist state. Thus, a high triplet energy level is achieved, and high efficiency is achieved.

(Device Manufacturing Example 2)

An organic electroluminescence device of Example 11 was manufactured using Compound 2 as a material of an electron blocking layer.

[Example Compound]

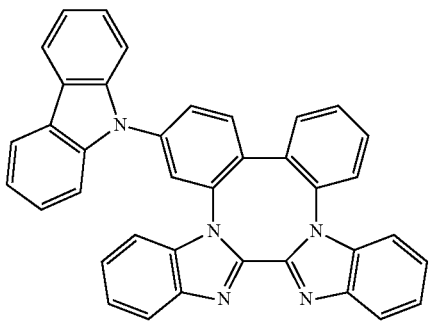

2

Organic electroluminescence devices of Comparative Examples 5 and 6 were manufactured using Comparative Compounds mCP and X-2 as materials of an electron blocking layer.

[Comparative Compounds]

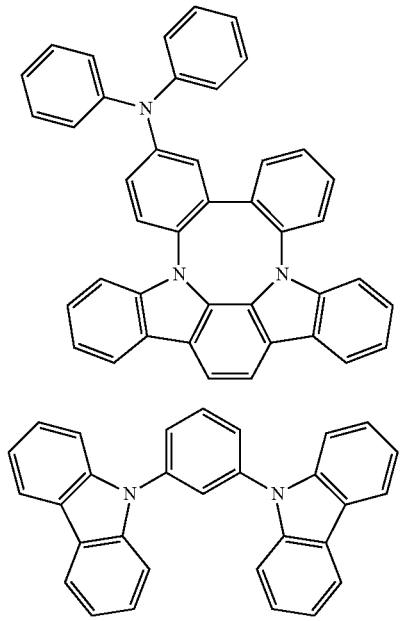

X-2 mCP

The organic electroluminescence devices of Example 11, and Comparative Examples 5 and 6 were manufactured as follows. A first electrode with a thickness of about 150 nm was formed using ITO, a hole injection layer with a thickness of about 10 nm was formed using HAT-CN, a hole transport layer with a thickness of about 80 nm was formed using α-NPD, an electron blocking layer with a thickness of about 5 nm was formed using the example compound or the comparative compound, an emission layer with a thickness of about 20 nm was formed using DPEPO doped with 18% ACRSA, a hole blocking layer with a thickness of about 10 nm was formed using DPEPO, an electron transport layer with a thickness of about 30 nm was formed using TPBi, an electron injection layer with a thickness of about 0.5 nm was formed using LiF, and a second electrode with a thickness of about 100 nm was formed using Al. Each layer was formed by a vacuum deposition method

TABLE 2

| | Electron blocking layer material | Maximum emission efficiency |
|---|---|---|
| Example 11 | Example Compound 2 | 130% |
| Comparative Example 5 | mCP | 100% |
| Comparative Example 6 | Comparative Compound X-2 | 100% |

The evaluation of the emission properties of the organic electroluminescence devices thus manufactured were measured using a C9920-12 brightness light distribution characteristics measurement system manufactured by HAMAMATSU Photonics Co.

Referring to Table 2, the compound including nitrogen according to an embodiment of the present disclosure may be used in a hole transport region, may restrain the diffusion of excitons to neighboring layers due to a high triplet energy level, and attains high efficiency when compared to the comparative examples.

The compound including nitrogen according to an embodiment of the present disclosure may be used as a material of an organic layer of an organic electroluminescence device, and by using the compound, the efficiency of the organic electroluminescence device may be improved.

The terminology used herein is for the purpose of describing particular embodiments only and is not intended to be limiting of the present disclosure. As used herein, the term "and/or" includes any and all combinations of one or more of the associated listed items. Expressions such as "at least one of," when preceding a list of elements, modify the entire list of elements and do not modify the individual elements of the list.

As used herein, the terms "substantially," "about," and similar terms are used as terms of approximation and not as terms of degree, and are intended to account for the inherent deviations in measured or calculated values that would be recognized by those of ordinary skill in the art. Further, the use of "may" when describing embodiments of the present disclosure refers to "one or more embodiments of the present disclosure." As used herein, the terms "use," "using," and "used" may be considered synonymous with the terms "utilize," "utilizing," and "utilized," respectively. Also, the term "exemplary" is intended to refer to an example or illustration.

Also, any numerical range recited herein is intended to include all sub-ranges of the same numerical precision subsumed within the recited range. For example, a range of "1.0 to 10.0" is intended to include all subranges between (and including) the recited minimum value of 1.0 and the recited maximum value of 10.0, that is, having a minimum value equal to or greater than 1.0 and a maximum value equal to or less than 10.0, such as, for example, 2.4 to 7.6. Any maximum numerical limitation recited herein is intended to include all lower numerical limitations subsumed therein, and any minimum numerical limitation recited in this specification is intended to include all higher numerical limitations subsumed therein. Accordingly, Applicant reserves the right to amend this specification, including the claims, to expressly recite any sub-range subsumed within the ranges expressly recited herein.

Although the exemplary embodiments of the present disclosure have been described, it is understood that the subject matter of the present disclosure should not be limited to these exemplary embodiments but various changes and modifications can be made by one ordinary skilled in the art within the spirit and scope of the subject matter of the present disclosure as hereinafter claimed.

What is claimed is:

1. A compound including nitrogen, represented by the following Formula 1:

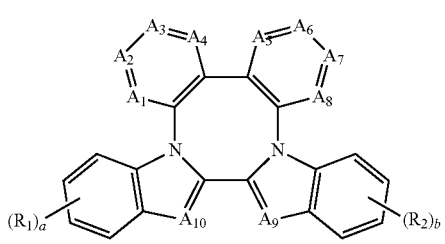

Formula 1 wherein in Formula 1, $A_1$ to $A_{10}$ are each independently $CR_3$ or N, $R_1$ to $R_3$ are each independently a hydrogen atom, a deuterium atom, a halogen atom, a cyano group, a substituted or unsubstituted amino group, a substituted or unsubstituted silyl group, a substituted or unsubstituted phosphine group, a substituted or unsubstituted alkyl group having 1 to 20 carbon atoms, a substituted or unsubstituted aryl group having 6 to 30 carbon atoms for forming the aryl ring of the aryl group, or a substituted or unsubstituted heteroaryl group having 2 to 30 carbon atoms for forming the heteroaryl ring of the heteroaryl, a and b are each independently an integer of 0 to 4, and wherein:

at least one of $A_9$ and $A_{10}$ is $CR_3$, or at least one of $A_1$ to $A_8$ is $CR_3'$, and $R_3'$ is a halogen atom, a cyano group, a substituted or unsubstituted amino group, a substituted or unsubstituted silyl group, a substituted or unsubstituted phosphine group, a substituted or unsubstituted alkyl group having 1 to 20 carbon atoms, or a substituted or unsubstituted heteroaryl group having 2 to 30 carbon atoms for forming the heteroaryl ring of the heteroaryl, or at least one of $A_1$ to $A_8$ is N.

2. The compound including nitrogen of claim 1, wherein the number of nitrogen atoms (N) among $A_1$ to $A_8$ is 0, 1, or 2.

3. The compound including nitrogen of claim 1, wherein $A_9$ and $A_{10}$ are the same.

4. The compound including nitrogen of claim 1, wherein $R_3$ is a fluorine atom, a cyano group, a substituted or unsubstituted arylamino group, a substituted or unsubstituted triphenylsilyl group, a substituted or unsubstituted diphenylphosphine oxide group, a substituted or unsubstituted alkyl group having 1 to 5 carbon atoms, a substituted or unsubstituted phenyl group, a substituted or unsubstituted pyridine group, a substituted or unsubstituted triazine group, a substituted or unsubstituted carbazole group, a substituted or unsubstituted dibenzofuran group, or a substituted or unsubstituted dibenzothiophene group.

5. The compound including nitrogen of claim 1, wherein $A_9$ and $A_{10}$ are nitrogen atoms (N).

6. The compound including nitrogen of claim 1, wherein $A_9$ and $A_{10}$ are each independently $CR_3$, and $R_3$ is a hydrogen atom, a substituted or unsubstituted alkyl group having 1 to 5 carbon atoms, or a substituted or unsubstituted phenyl group.

7. The compound including nitrogen of claim 1, wherein a and b are 0.

8. The compound including nitrogen of claim 1, wherein at least one of a or b is 1 or more, and at least one of $R_1$ or $R_2$ is a fluorine atom, a cyano group, a substituted or unsubstituted arylamino group, a substituted or unsubstituted triphenylsilyl group, a substituted or unsubstituted diphenylphosphine oxide group, a substituted or unsubstituted phenyl group, a substituted or unsubstituted pyridine group, a substituted or unsubstituted triazine group, a substituted or unsubstituted carbazole group, a substituted or unsubstituted dibenzofuran group, or a substituted or unsubstituted dibenzothiophene group.

9. The compound including nitrogen of claim 1, wherein the compound including nitrogen, represented by Formula 1 is one selected from compounds represented in the following Compound Group 1:

[Compound Group 1]

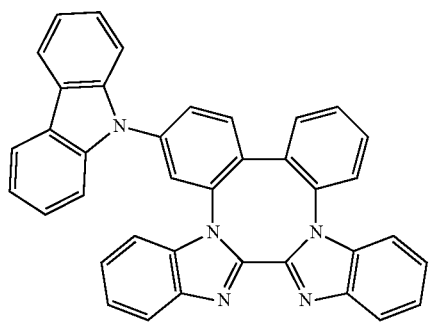

2

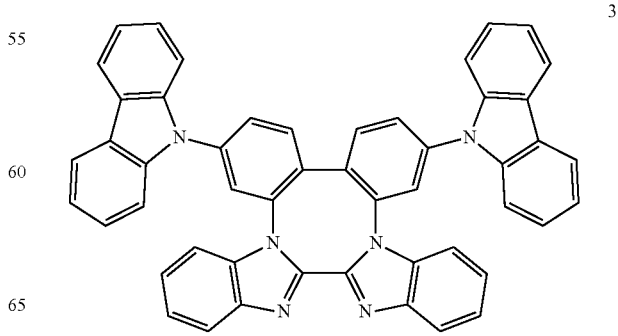

3

4
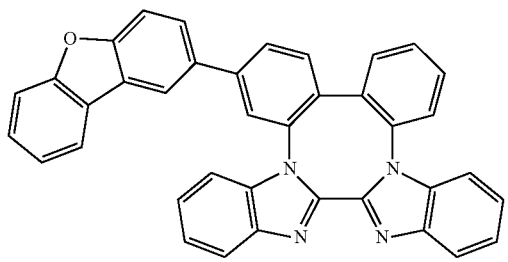
5
6
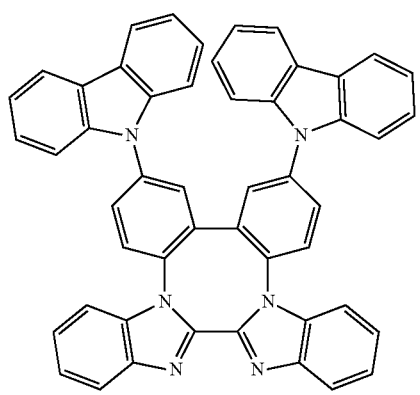
7
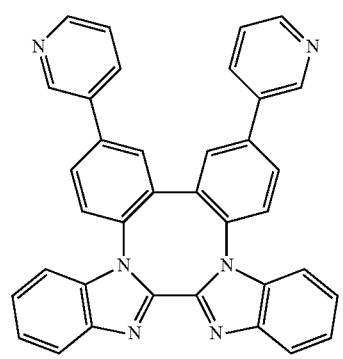
8
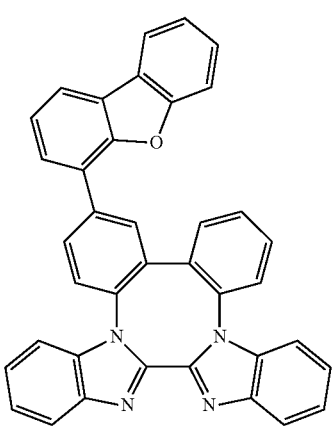
9
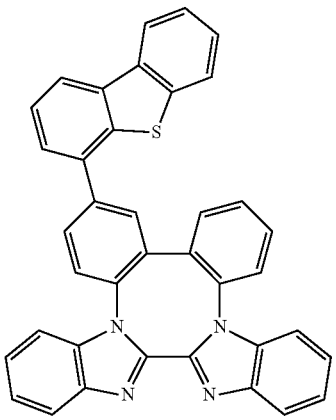
10
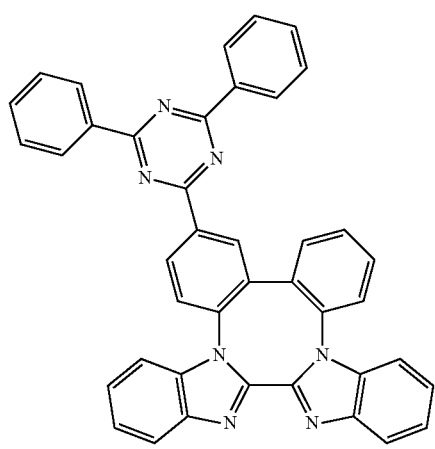
11
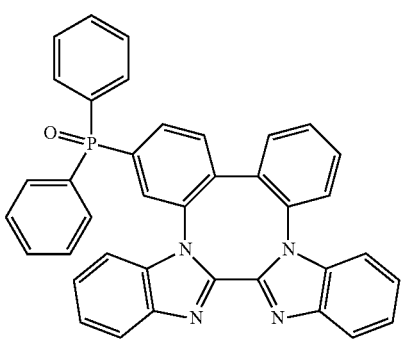
12
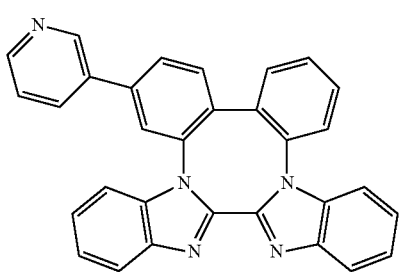

13
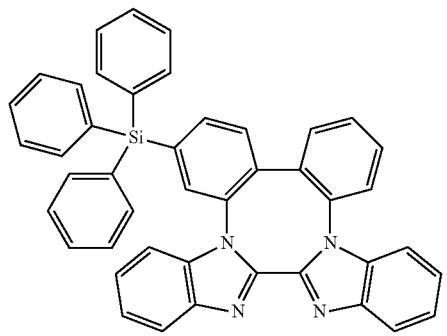
14
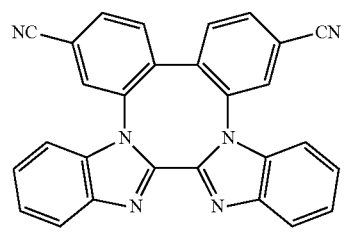
15
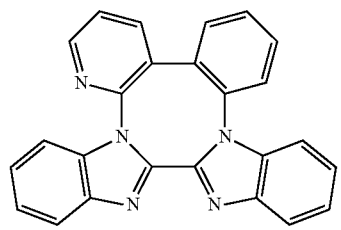
16
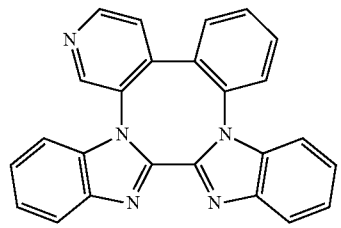
17
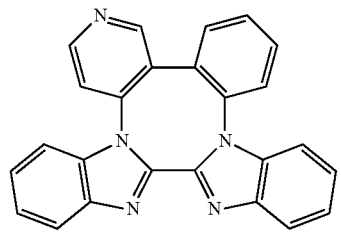
18
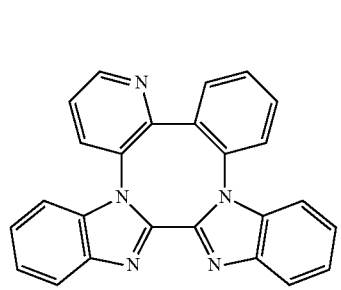
19
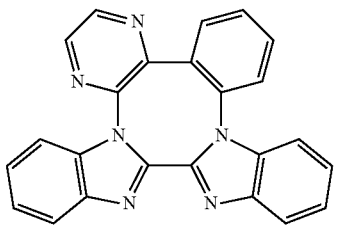
20
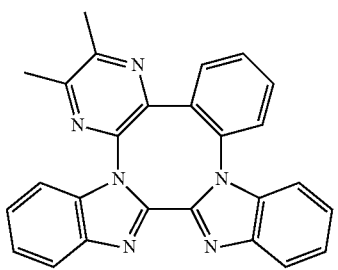
21
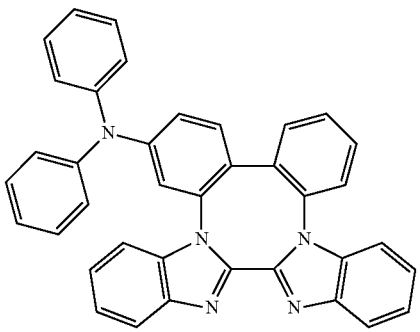
22
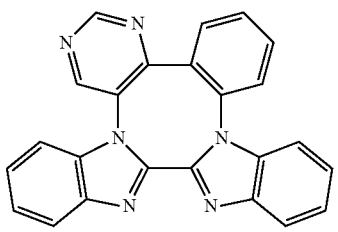
23
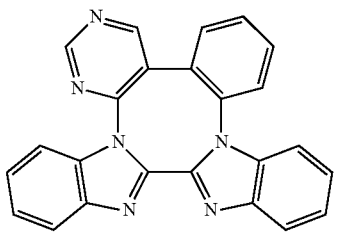
24
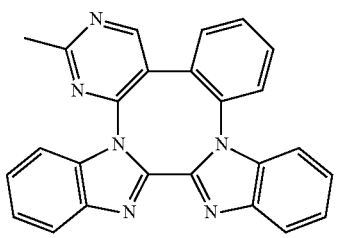

25
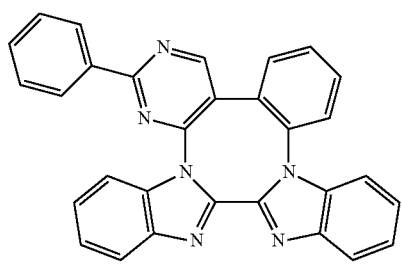
26
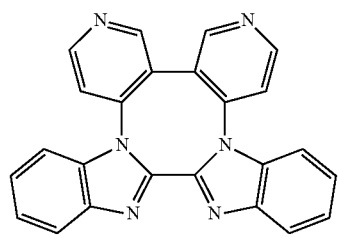
27
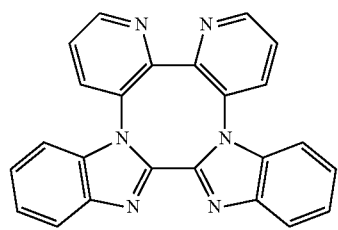
28
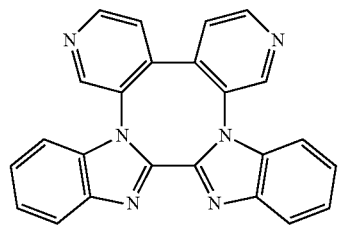
29
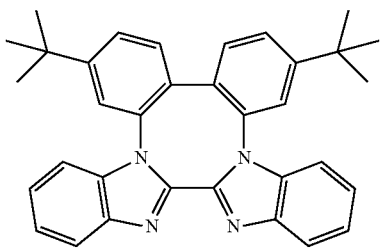
30
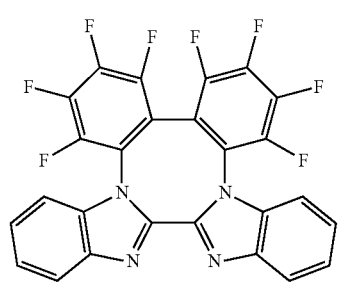
31
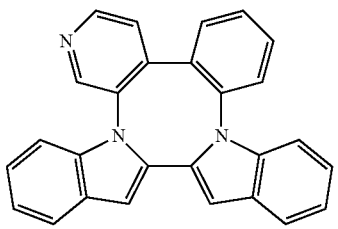
32
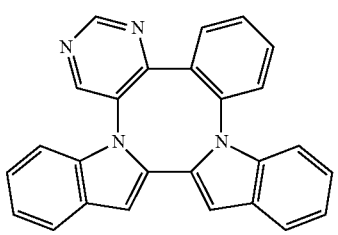
33
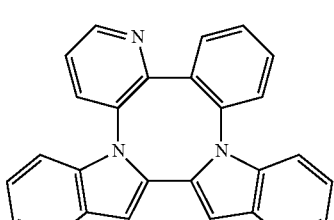
34
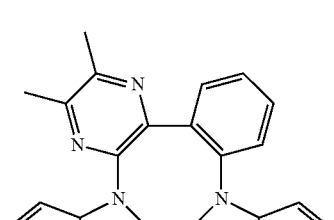
35
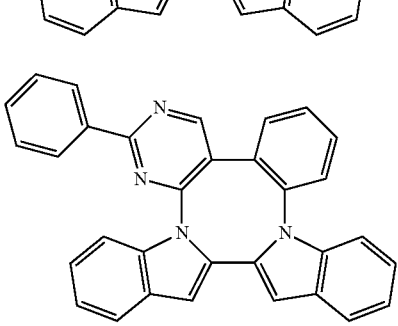
36
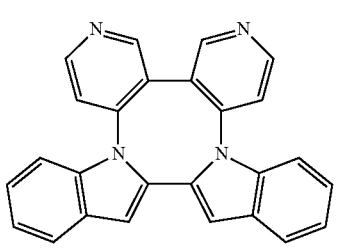

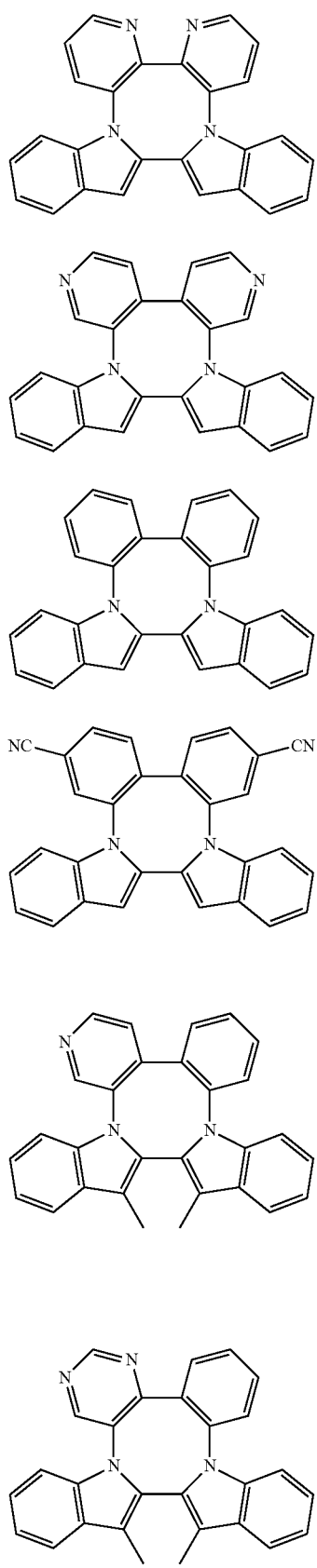
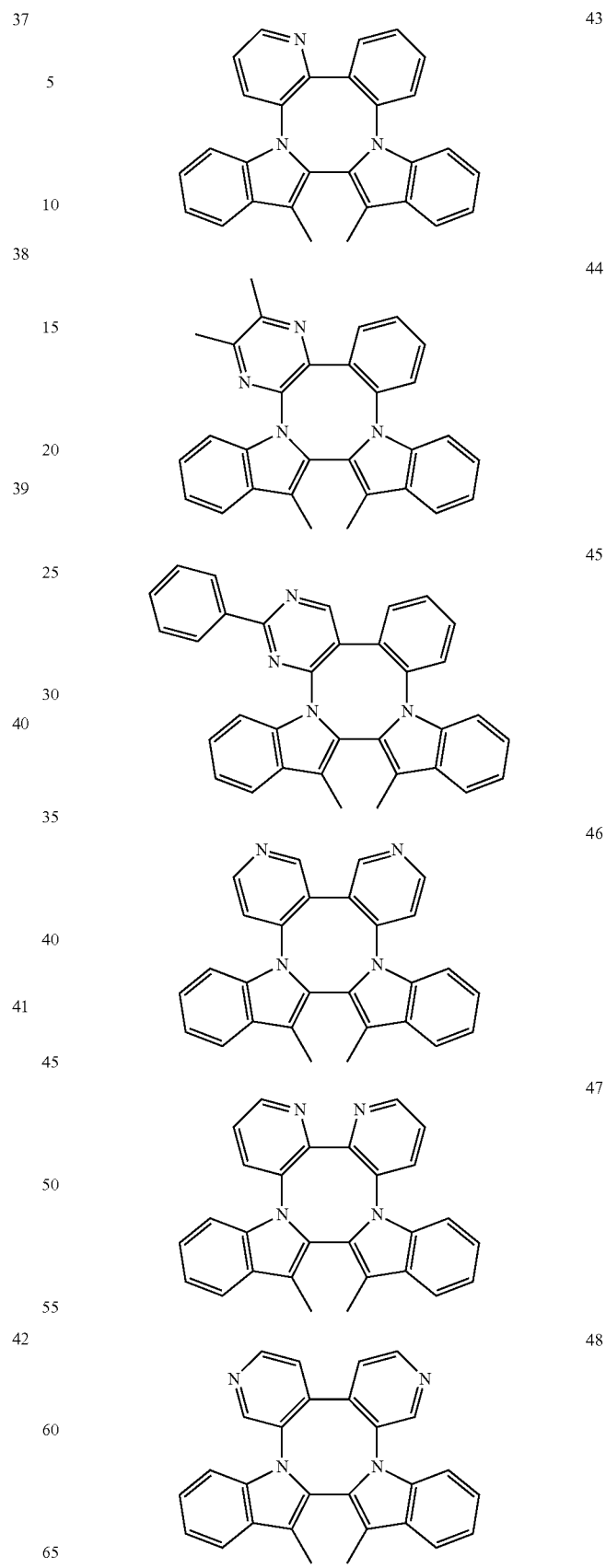

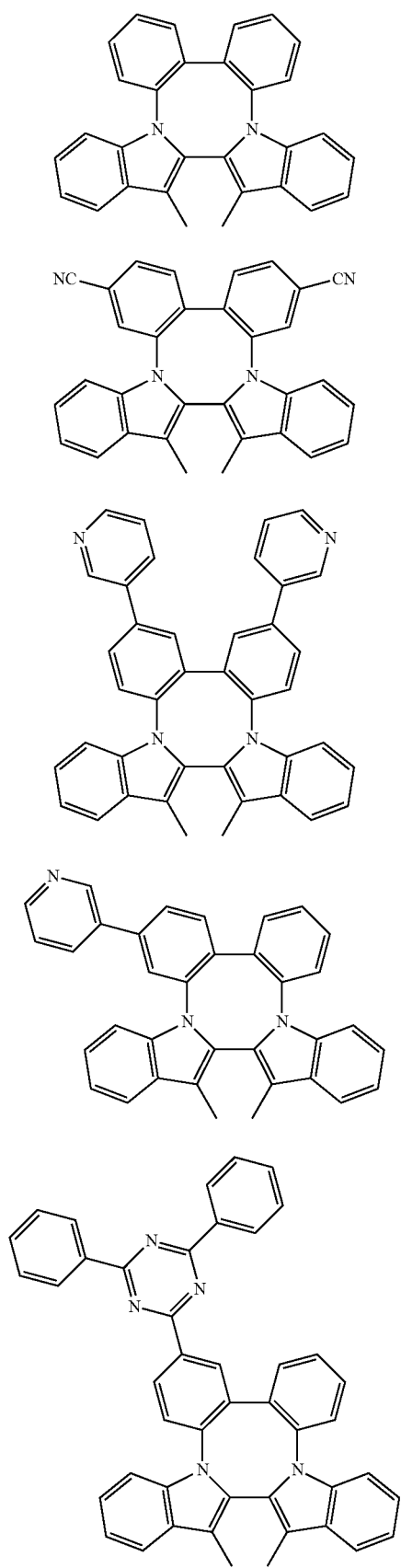
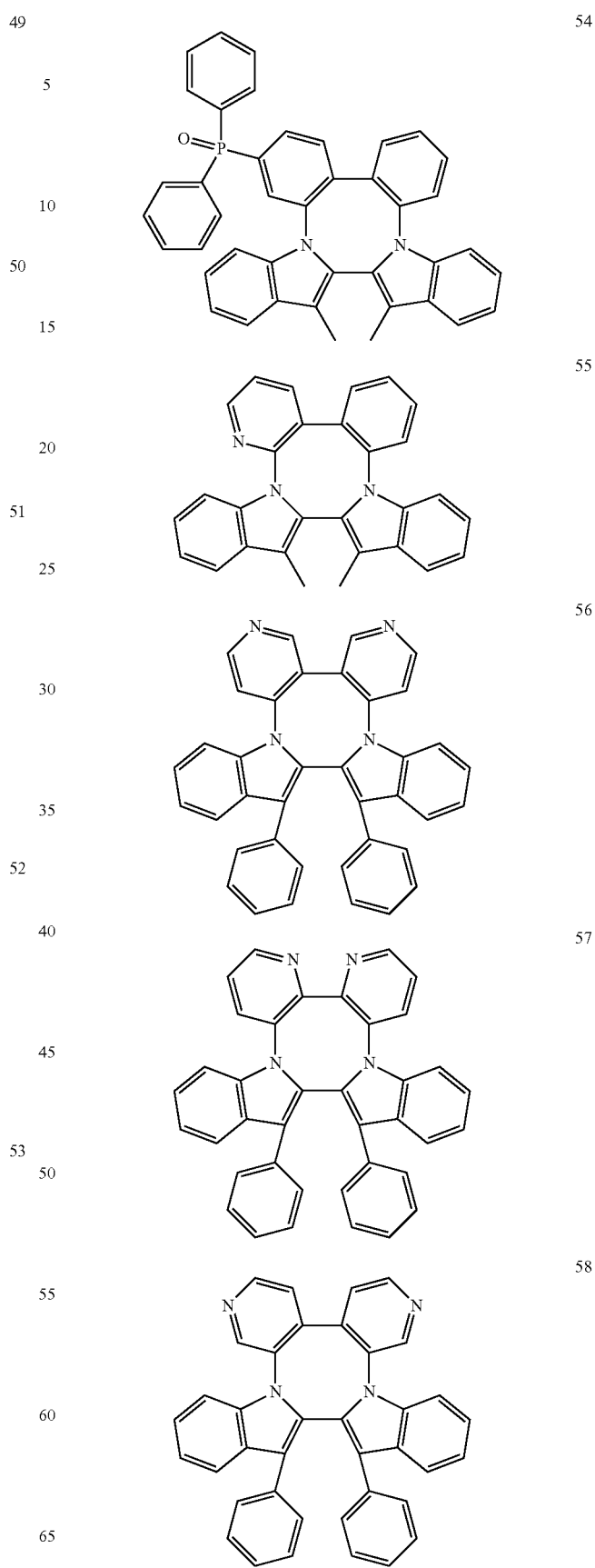

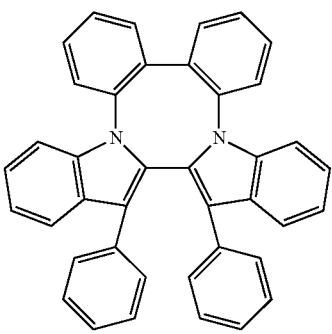

59

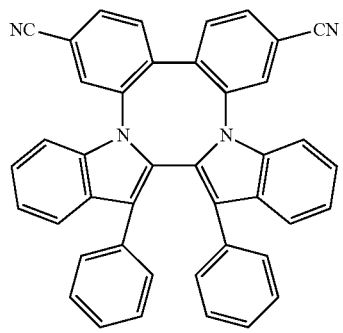

60

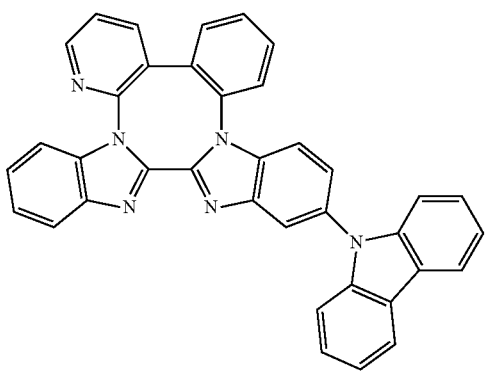

78

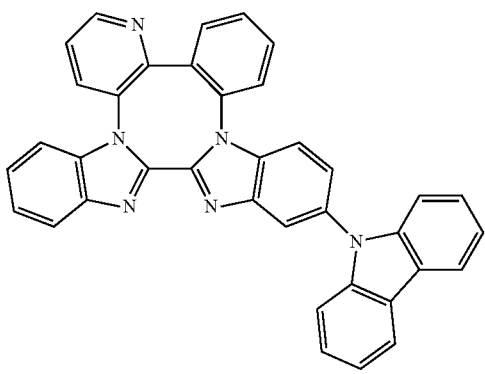

79

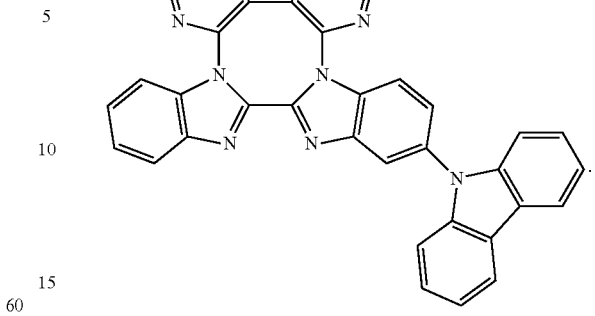

80

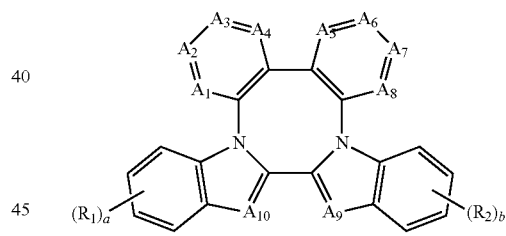

10. An organic electroluminescence device, comprising:
a first electrode;
a second electrode which is opposite to the first electrode; and
a plurality of organic layers disposed between the first electrode and the second electrode, the plurality of organic layers comprising an emission layer,
wherein the first electrode and the second electrode each independently comprise at least one selected from Ag, Mg, Cu, Al, Pt, Pd, Au, Ni, Nd, Ir, Cr, Li, Ca, LiF/Ca, LiF/Al, Mo, Ti, In, Sn, and Zn, or a compound of two or more selected from them, a mixture of two or more selected from them, or oxides of one or more selected from them,
wherein at least one organic layer among the organic layers comprises a compound including nitrogen, represented by the following Formula 1:

[Formula 1]

wherein in Formula 1,
$A_1$ to $A_{10}$ are each independently $CR_3$ or N,
$R_1$ to $R_3$ are each independently a hydrogen atom, a deuterium atom, a halogen atom, a cyano group, a substituted or unsubstituted amino group, a substituted or unsubstituted silyl group, a substituted or unsubstituted phosphine group, a substituted or unsubstituted alkyl group having 1 to 20 carbon atoms, a substituted or unsubstituted aryl group having 6 to 30 carbon atoms for forming the aryl ring of the aryl group, or a substituted or unsubstituted heteroaryl group having 2 to 30 carbon atoms for forming the heteroaryl ring of the heteroaryl group, and
a and b are each independently an integer of 0 to 4.

11. The organic electroluminescence device of claim 10, wherein the emission layer comprises the compound including nitrogen, represented by Formula 1.

12. The organic electroluminescence device of claim 10, wherein the emission layer comprises a host and a dopant, and the host comprises the compound including nitrogen, represented by Formula 1.

13. The organic electroluminescence device of claim 10, wherein the organic layers comprise:
a hole transport region disposed between the first electrode and the emission layer; and
an electron transport region disposed between the emission layer and the second electrode,
wherein the hole transport region comprises the compound including nitrogen, represented by Formula 1.

14. The organic electroluminescence device of claim 10, wherein the number of nitrogen atoms (N) among $A_1$ to $A_8$ is 0, 1, or 2.

15. The organic electroluminescence device of claim 10, wherein $A_9$ and $A_{10}$ are the same.

16. The organic electroluminescence device of claim 10, wherein:
at least one of $A_1$ to $A_8$ is $CR_3$ or N, and
$R_3$ is a fluorine atom, a cyano group, a substituted or unsubstituted arylamino group, a substituted or unsubstituted triphenylsilyl group, a substituted or unsubstituted diphenylphosphine oxide group, a substituted or unsubstituted alkyl group having 1 to 5 carbon atoms, a substituted or unsubstituted phenyl group, a substituted or unsubstituted pyridine group, a substituted or unsubstituted triazine group, a substituted or unsubstituted carbazole group, a substituted or unsubstituted dibenzofuran group, or a substituted or unsubstituted dibenzothiophene group.

17. The organic electroluminescence device of claim 10, wherein $A_9$ and $A_{10}$ are nitrogen atoms (N).

18. The organic electroluminescence device of claim 10, wherein $A_9$ and $A_{10}$ are each independently $CR_3$, and
$R_3$ is a hydrogen atom, a substituted or unsubstituted alkyl group having 1 to 5 carbon atoms, or a substituted or unsubstituted phenyl group.

19. The organic electroluminescence device of claim 10, wherein a and b are 0.

20. The organic electroluminescence device of claim 10, wherein at least one of a or b is 1 or more, and
at least one of $R_1$ or $R_2$ is a fluorine atom, a cyano group, a substituted or unsubstituted arylamino group, a substituted or unsubstituted triphenylsilyl group, a substituted or unsubstituted diphenylphosphine oxide group, a substituted or unsubstituted phenyl group, a substituted or unsubstituted pyridine group, a substituted or unsubstituted triazine group, a substituted or unsubstituted carbazole group, a substituted or unsubstituted dibenzofuran group, or a substituted or unsubstituted dibenzothiophene group.

21. The organic electroluminescence device of claim 10, wherein the compound including nitrogen, represented by Formula 1 is at least one selected from compounds represented in the following Compound Group 1:

[Compound Group 1]

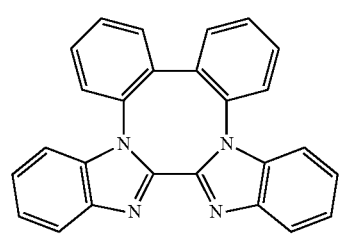

1

-continued

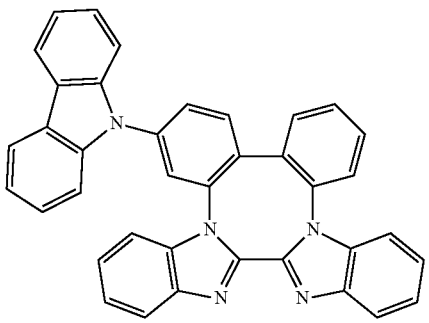

2

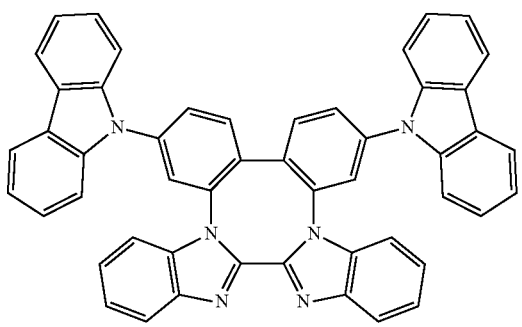

3

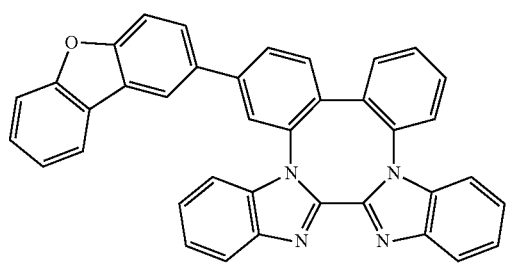

4

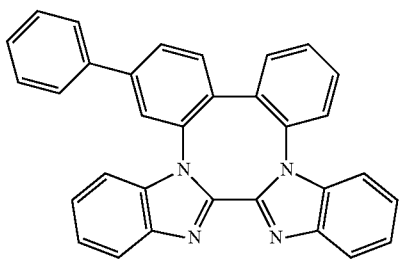

5

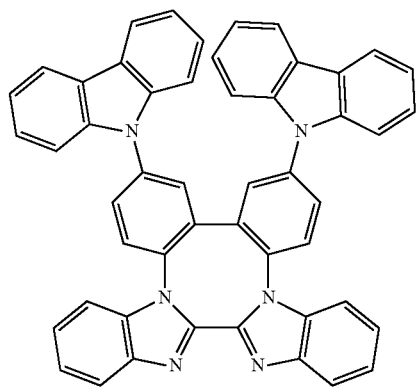

6

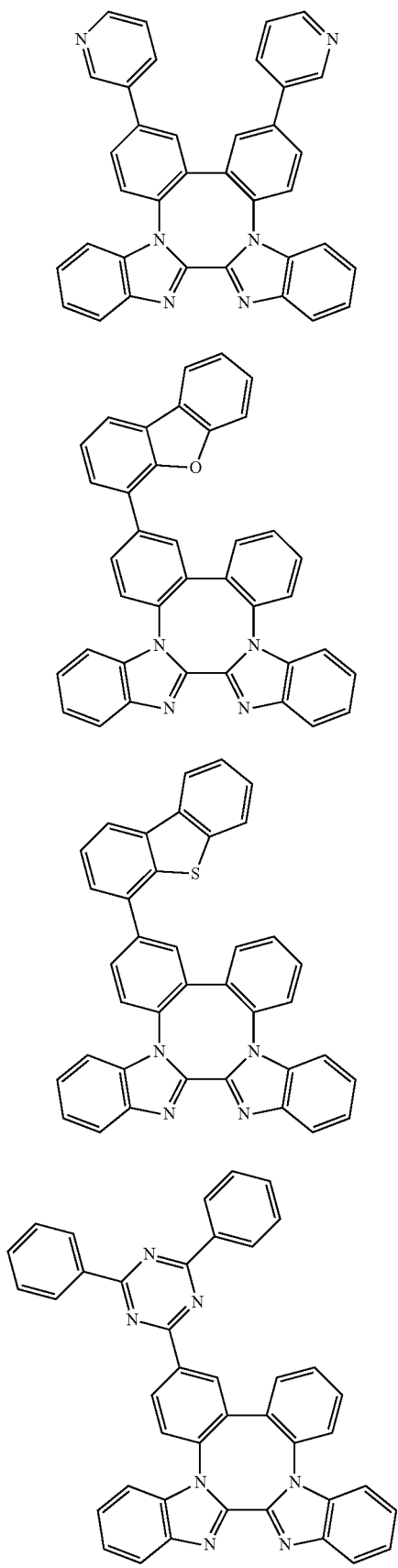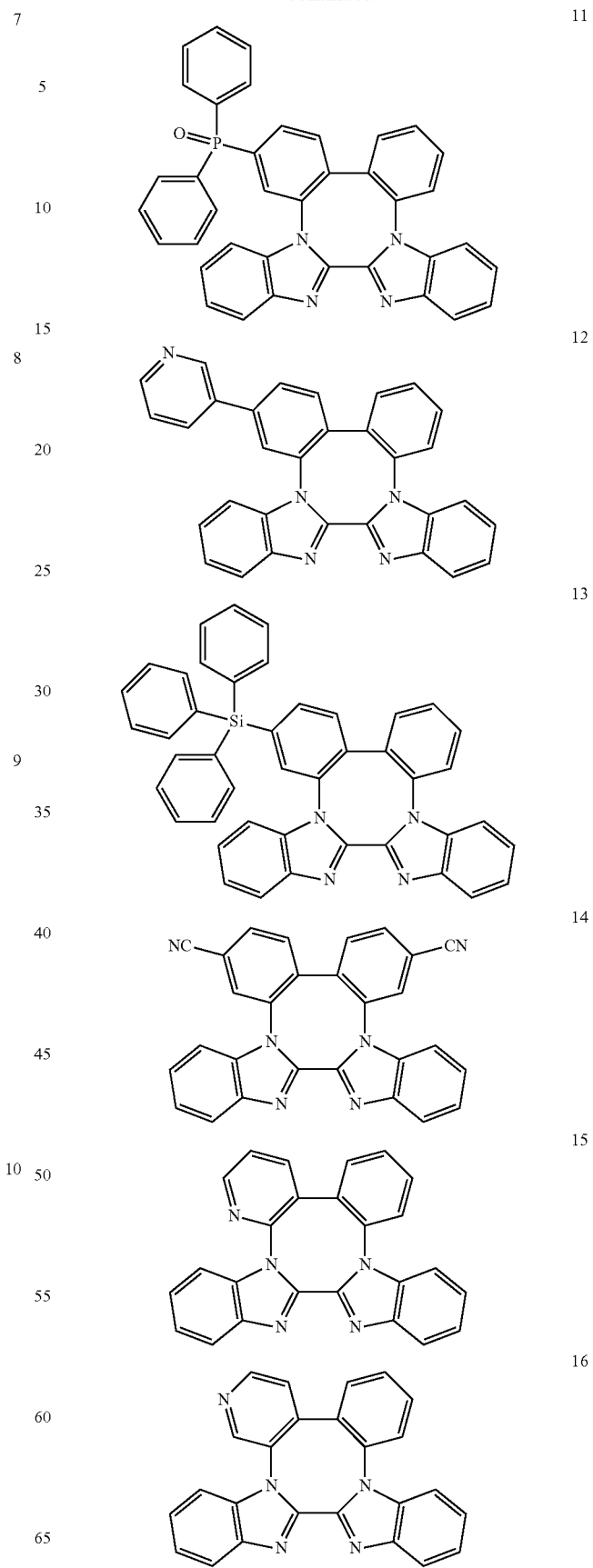

17
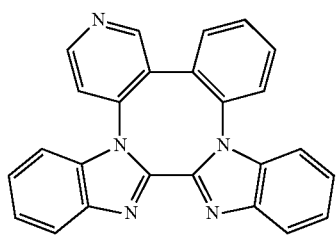
18
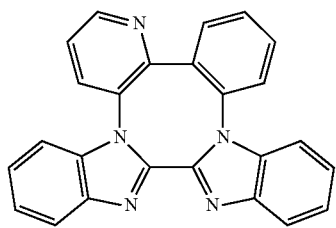
19
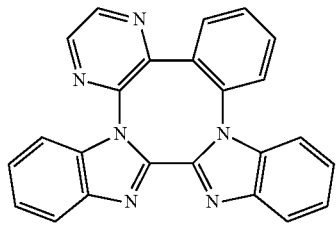
20
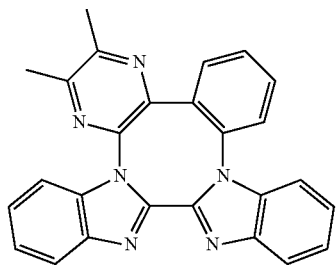
21
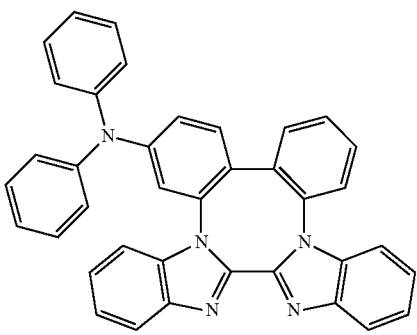
22
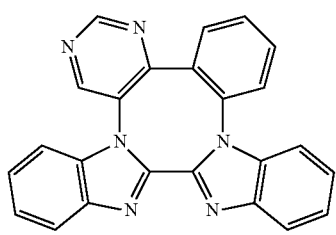
23
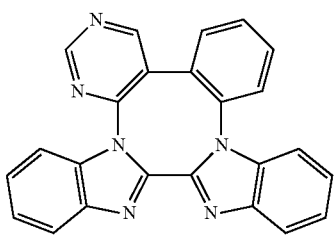
24
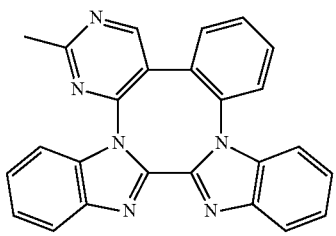
25
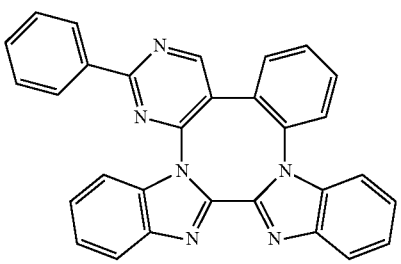
26
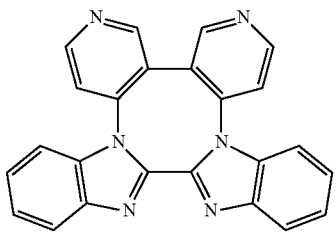
27
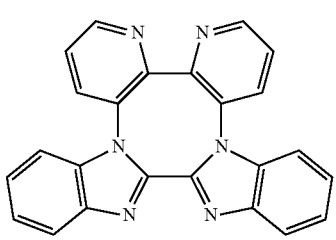
28
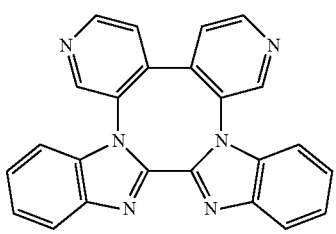

29
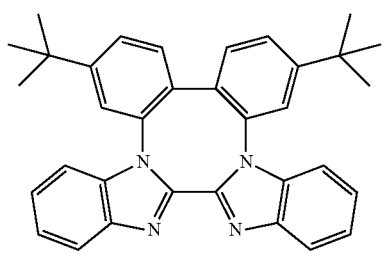
30
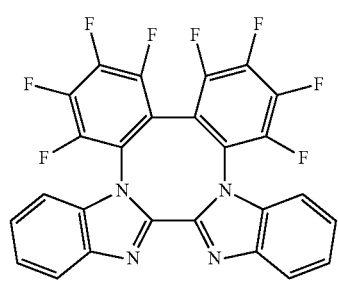
31
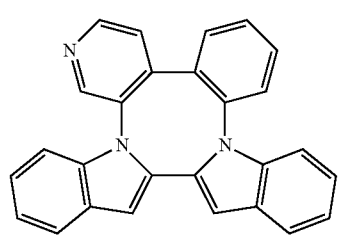
32
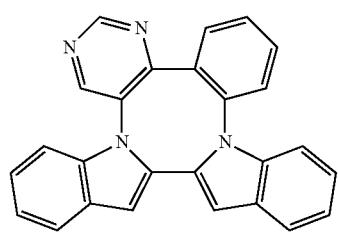
33
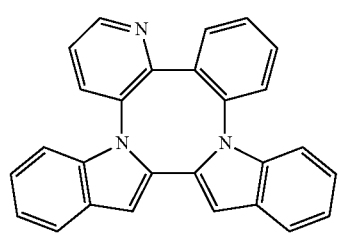
34
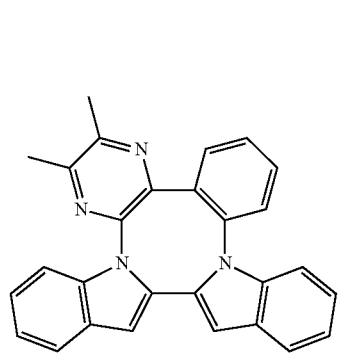
35
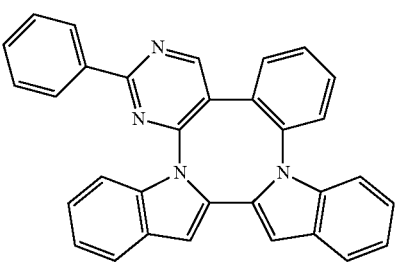
36
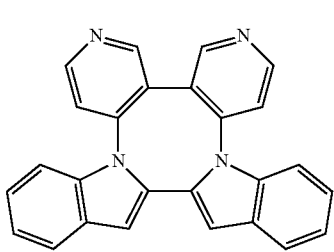
37
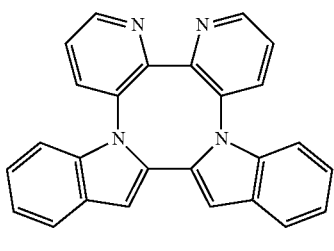
38
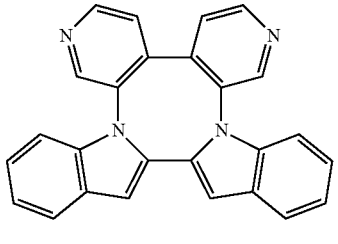
39
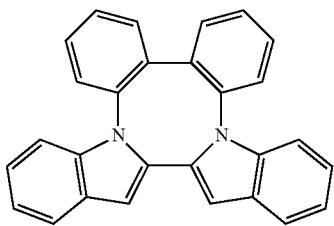
40
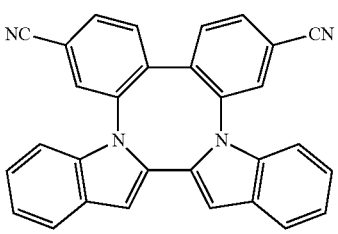

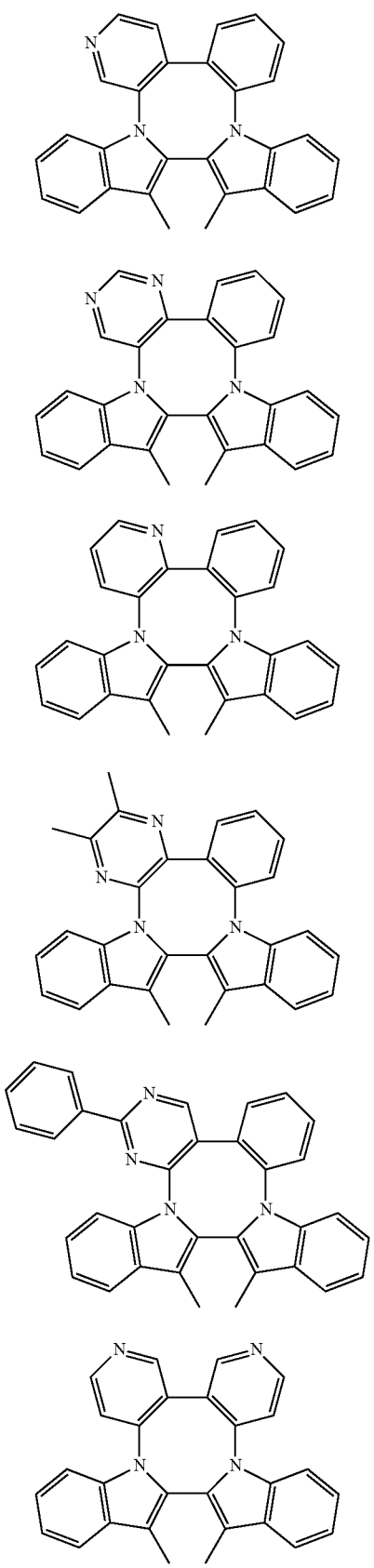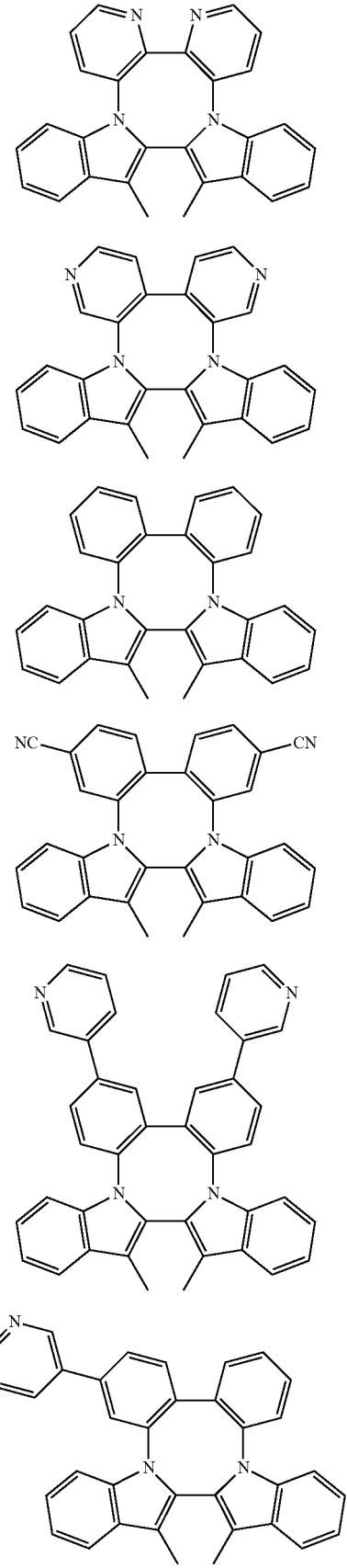

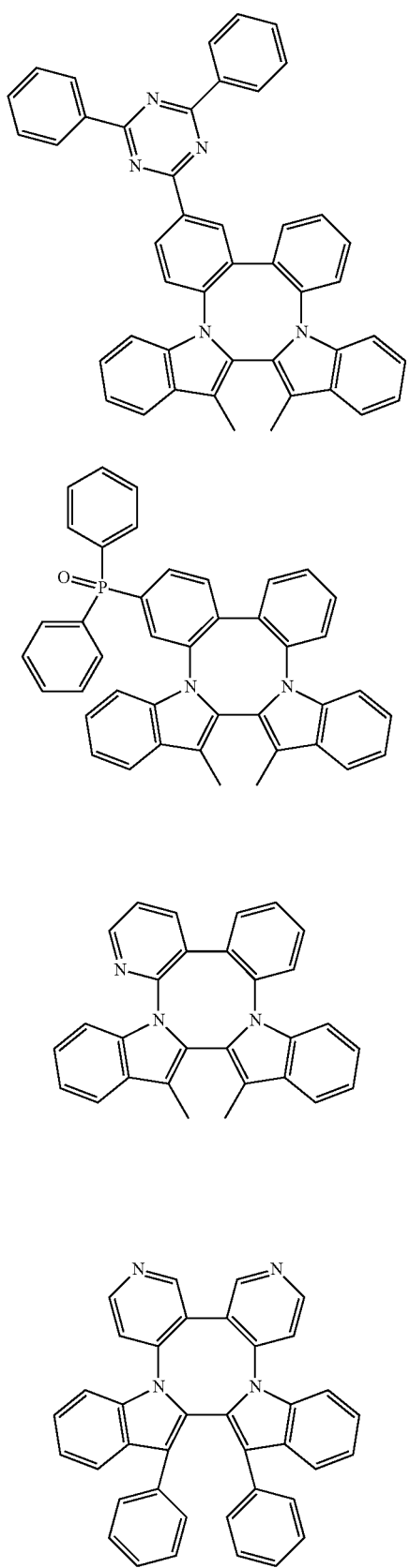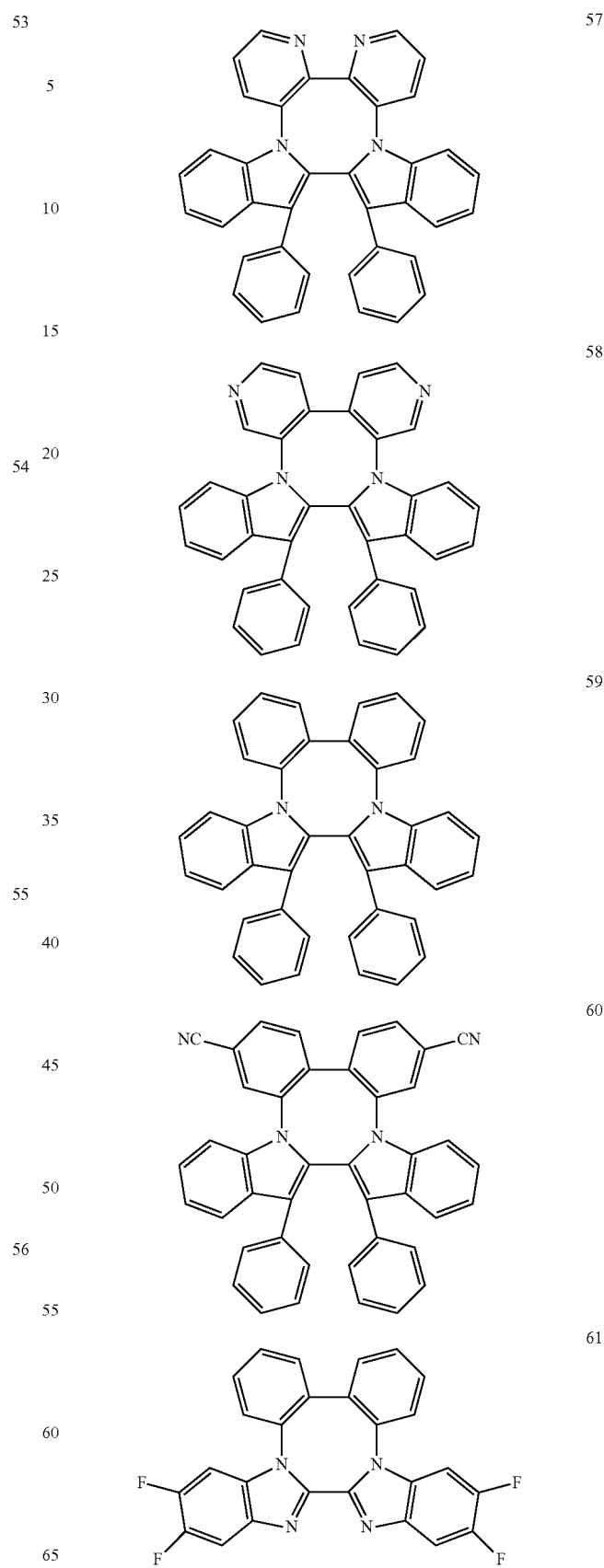

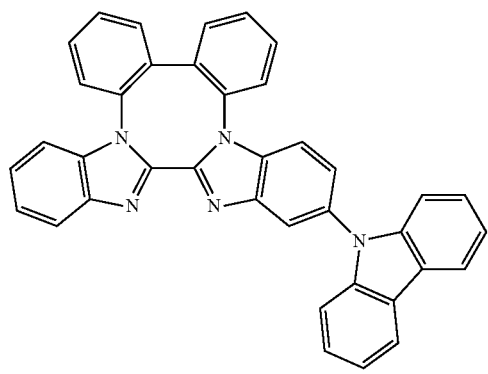
62
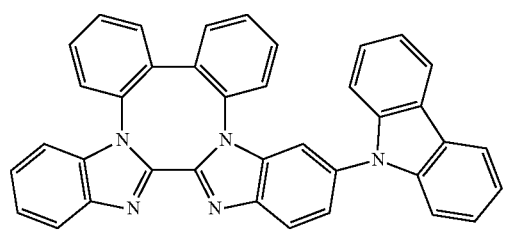
63
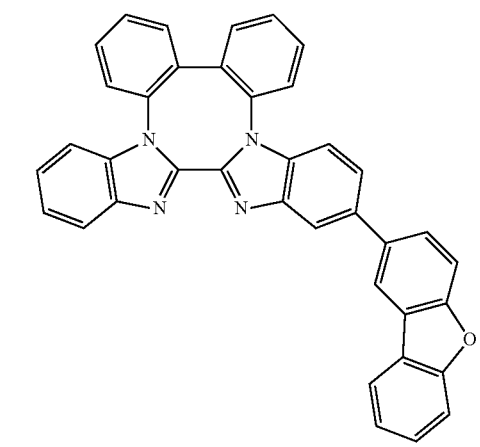
64
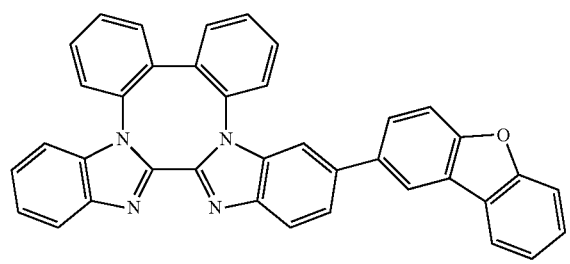
65
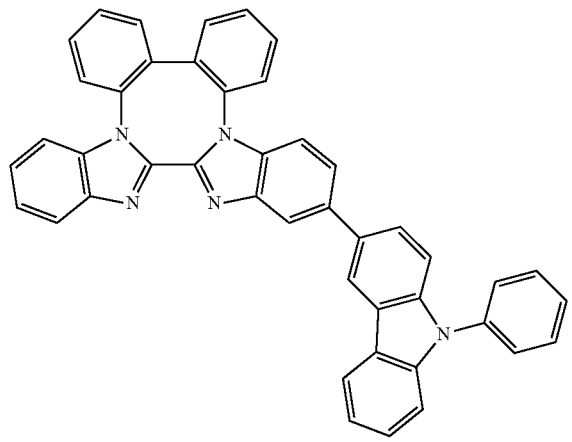
66
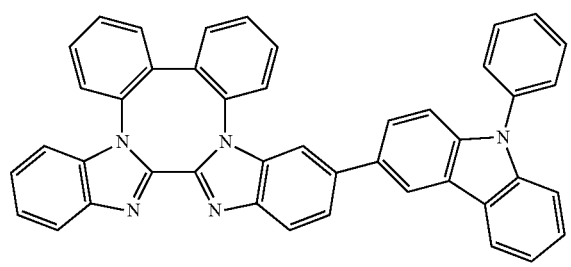
67
68
69
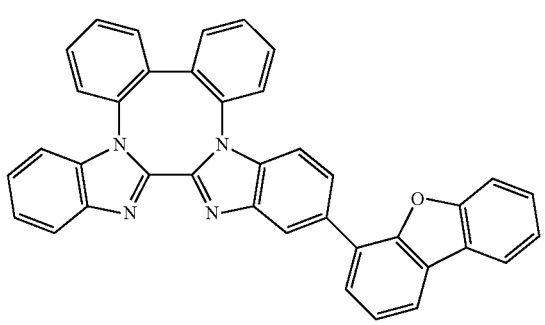
70

75
-continued
71
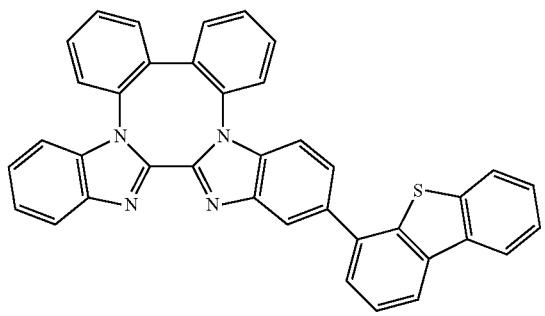
72
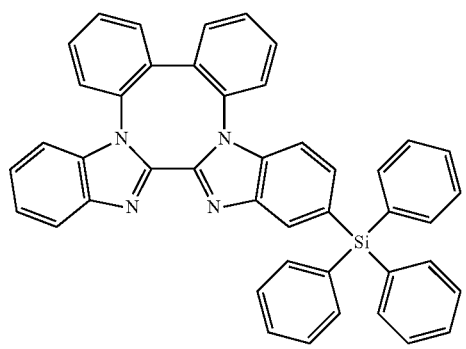
73
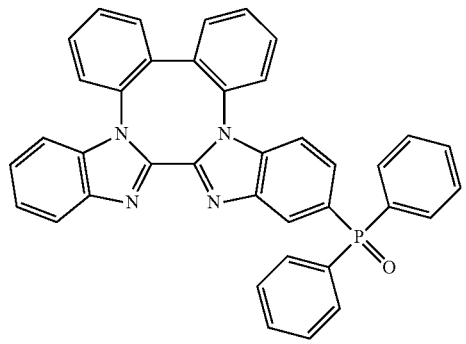
74
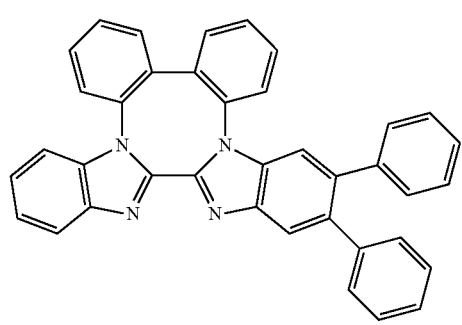
75
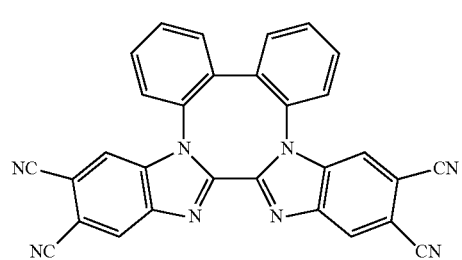
76
-continued
76
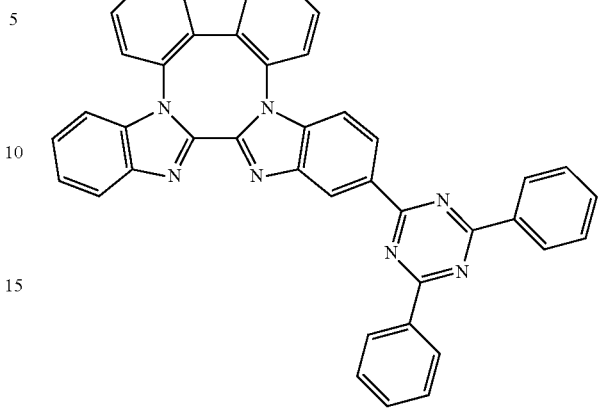
77
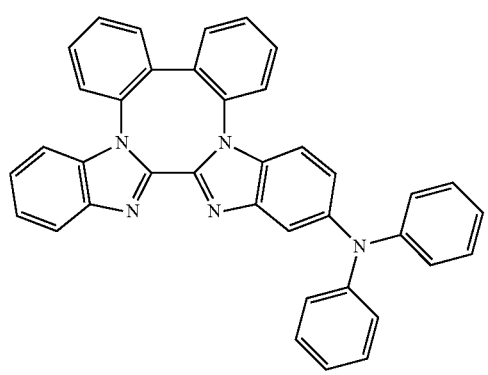
78
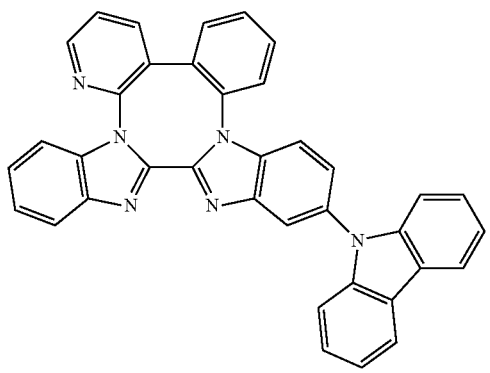
79
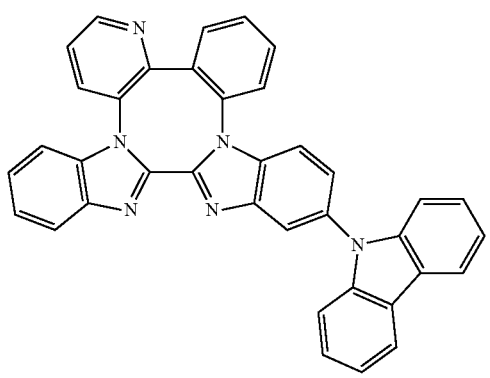

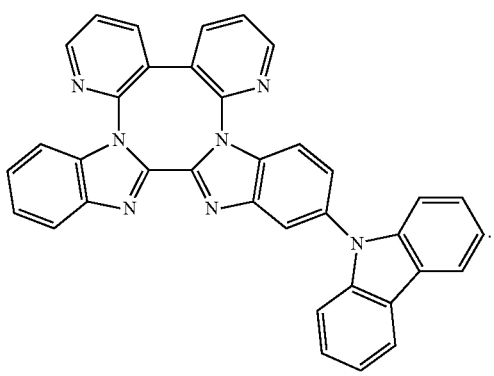
* * * * *